United States Patent [19]

Nakahara et al.

[11] 4,336,183
[45] Jun. 22, 1982

[54] 2,2,6,6-TETRAMETHYL-4-PIPERIDYL CARBOXYLIC ACID ESTERS AND AMIDES OF MONO AND POLY ALCOHOLS, PHENOLS AND AMINES AS STABILIZERS FOR SYNTHETIC POLYMERS

[75] Inventors: Yutaka Nakahara, Iwatsuki; Toshihiro Shibata, Omiya; Naohiro Kubota, Ageo, all of Japan

[73] Assignee: Adeka Argus Chemical Co., Ltd., Urawa, Japan

[21] Appl. No.: 178,202

[22] Filed: Aug. 14, 1980

Related U.S. Application Data

[63] Continuation-in-part of Ser. No. 167,889, Jul. 14, 1980.

[30] Foreign Application Priority Data

Jul. 12, 1979 [JP] Japan .................................. 54/88474

[51] Int. Cl.$^3$ ................ C07D 491/113; C07D 498/10; C08K 5/35
[52] U.S. Cl. ..................................... 524/95; 546/19; 524/100; 524/101; 524/102; 524/103; 544/71; 544/230; 544/198; 544/222
[58] Field of Search ................... 260/45.8 NZ; 546/19

[56] References Cited

U.S. PATENT DOCUMENTS

| | | | |
|---|---|---|---|
| 3,431,233 | 3/1969 | Murayama et al. | 260/45.8 NZ |
| 3,692,778 | 9/1972 | Murayama et al. | 260/45.8 NZ |
| 4,007,158 | 2/1977 | Murayama et al. | 260/45.8 NZ |
| 4,105,625 | 8/1978 | Minagawa et al. | 546/19 |
| 4,128,608 | 12/1978 | Minagawa et al. | 260/45.8 NZ |
| 4,237,294 | 12/1980 | Soma et al. | 546/19 |

Primary Examiner—John Kight, III
Assistant Examiner—R. A. White

[57] ABSTRACT 2,2,6,6-Tetramethyl-4-piperidyl carboxylic acid esters and amides of mono and poly alcohols, phenols and amines are provided, useful as stabilizers for organic polymeric materials, and having the general formula:

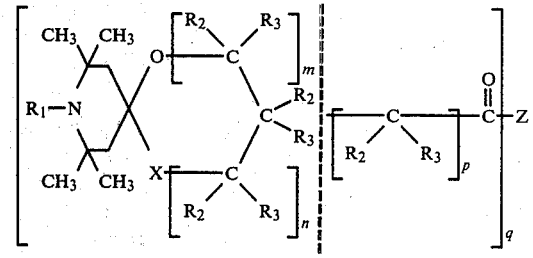

33 Claims, No Drawings

2,2,6,6-TETRAMETHYL-4-PIPERIDYL CARBOXYLIC ACID ESTERS AND AMIDES OF MONO AND POLY ALCOHOLS, PHENOLS AND AMINES AS STABILIZERS FOR SYNTHETIC POLYMERS

This application is a continuation-in-part of Ser. No. 167,889, filed July 14, 1980.

Hindered 2,2,6,6-tetraalkyl-4-carboxylic acid ester piperidine compounds having been proposed by Murayama et al. U.S. Pat. No. 3,640,928, patented Feb. 8, 1972 as light and heat stabilizers for synthetic polymers, such as polyolefins, polyvinyl chloride, polyvinylidene chloride, polyurethanes, and polyamides. These compounds have the general formula:

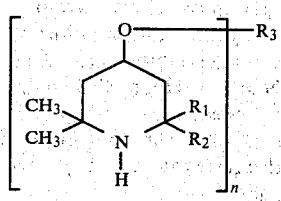

or a salt thereof.

In the above formula:

$R_1$ and $R_2$ which may be the same or different, each are an alkyl group such as methyl, ethyl, isopropyl or dodecyl, or they form, together with the carbon atom to which they are attached, a saturated alicyclic group such as:

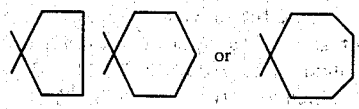

or a group of the formula

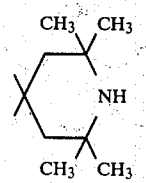

n is an integer of 1 to 3 inclusive; and $R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al No. 3,790,525, patented Feb. 5, 1974, provides synthetic polymer compositions stablized against photo-and thermal-deterioration incorporating in the composition an effective amount of a 4-piperidone ketal having the formulae:

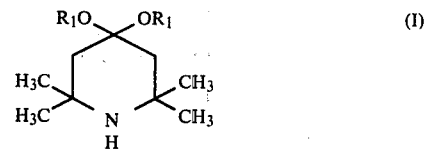

and

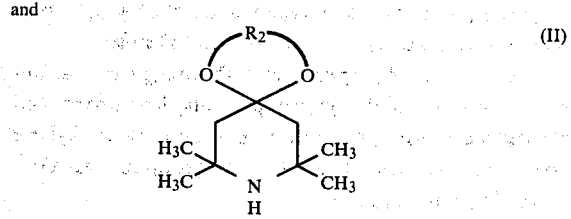

wherein $R_1$ represents an alkyl group of one to eight carbon atoms and $R_2$ represents an alkylene group of two or three carbon atoms or o-phenylene group.

Murayama et al No. 3,898,303 patented Aug. 5, 1975 propose piperidino-spiro-hydantoin derivatives having the formula:

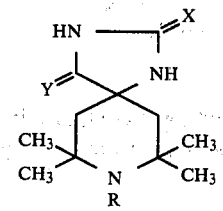

wherein:

R represents an alkyl group, an alkenyl group, an alkenoyl group which may be substituted with an aryl group, a hydroxyalkyl group, an alkoxy-alkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 discloses a variation of the piperidino spiro compounds having the formula:

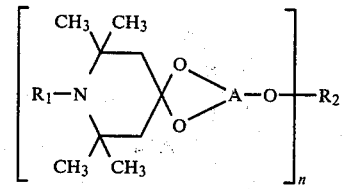

wherein:

$R_1$ represents hydrogen atom, an alkyl group, a substituted alkyl group, an alkenyl group, an alkynyl group, a substituted or unsubstituted aralkyl group, an aliphatic acyl group, an alkoxy-carbonyl group or an aralkoxycarbonyl group, n is an integer of 1 to 4;

when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N- substituted carbamoyl group, a N-substituted thiocarbamoyl group, a monovalent group from an oxoacid or group $$-\underset{\underset{R_3}{|}}{C}=CH-COOR_4$$

in which $R_3$ represents hydrogen atom, a lower alkyl group or phenyl group and $R_4$ represents an alkyl group;

when n is 2, $R_2$ represents carbonyl group, an aliphatic or aromatic diacyl group, an alkylene group, and alkenylene group, an alkynylene group, an aralkylene group, a N-substituted dicarbamoyl group or a divalent group from an oxoacid;

when n is 3, $R_2$ represents an aromatic triacyl group or a trivalent group from an oxoacid; and when n is 4, $R_2$ represents an aromatic tetraacyl group, and A represents a group $$\begin{matrix} -CH_2 & & R_5 \\ & \diagdown & \diagup \\ & C & \\ & \diagup & \diagdown \\ -CH_2 & & CH_2- \end{matrix}$$

in which $R_5$ represents hydrogen atom or a lower alkyl group or, when n is 1, $R_5$ may represent together with $R_2$ a group $$-CH_2-O\begin{matrix} CH_3 & CH_3 \\ \diagdown & \diagup \\ & \\ \diagup & \diagdown \\ CH_3 & CH_3 \end{matrix}N-R_6$$

in which $R_6$ represents the same group as defined in $R_1$ and may be the same or different from $R_1$, or a group $$\begin{matrix} & R_7 \\ & \diagup \\ -CH & \\ | & \\ -CH & \\ & \diagdown \\ & (CH_2)_m- \end{matrix}$$

in which m is 1 or 2 and $R_7$ represents hydrogen atom or, when n and m are 1, $R_7$ represents methylene group together with $R_2$.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744, patented Mar. 2, 1976 disclose another variation of the piperidino spiro derivatives having the formula:

$$R\left[\begin{matrix} & -N & X \\ & | & \diagup \\ Y= & & Z \\ CH_3 & & CH_3 \\ CH_3 & N & CH_3 \\ & | & \\ & R' & \end{matrix}\right]_n$$

wherein

R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula=N-R" in which R" is hydrogen atom, an alkyl group or a substituted alkyl group;

Z represents oxygen atom or a group of the formula >N-R''' is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene)-group, an alkylene-bis-(oxycarbonylalkyl)group, a dialkylene ether group or a diphenylene ether group, when n is 3, an alkanetriyl group, a tris-(acyloxyalkylene)-group, an alkane-tris-(oxycarbonylalkyl)group or a group of the group $$\begin{matrix} & (CH_2)_p- & \\ & | & \\ & N & \\ O= & & =O \\ & \diagup \diagdown & \\ -(CH_2)_p-N & & N-(CH_2)_p- \\ & \diagdown \diagup & \\ & C & \\ & \| & \\ & O & \end{matrix}$$

in which p is an integer 1 through 8 inclusive, and when n is 4, an alkane tetrayl group, a tetrakis-(acyloxyalkylene)-group or an alkanetetrakis-(oxycarbonylalkyl)group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

$$-(CH_2)_n-O-\overset{O}{\underset{\|}{C}}-X-\overset{O}{\underset{\|}{C}}-O-(CH_2)_n$$

in which n is an integer of 1 or 2 and X is an alkylene group, or o-, m- or p-phenylene group or the carbon atoms of CO groups may be directly joined in the absence of X or a group of the formula:

$$-CH_2-\overset{O}{\underset{\|}{C}}-O-Y-O-\overset{O}{\underset{\|}{C}}-CH_2$$

in which

Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperizines and substituted piperazinodiones. The substituted piperazines of U.S. Pat. No. 3,899,491 have the formula:

[Structure diagram showing piperazine with R¹, R² substituents and N—(CH₂)ₘ—CH(R⁴)—CO—R³ group]

wherein $R^1$ and $R^2$ are methyl or together with the carbon to which they are bound form a mono-cyclic ring system having five or six carbon atoms;

$R^3$ is an alkyl group of from one to twenty atoms;

$R^4$ is hydrogen or methyl, and m is 0 or 1.

The substituted piperazinodiones of No. 3,920,659 have the formula:

[Structure diagram showing piperazinodione with R¹, R² substituents and N—A—CO—R² group, bracketed with subscript n]

wherein $R^1$ and $R^2$ are independently of each other methyl or ethyl or together with the carbon to which they are bound form a cyclopentyl or cyclohexyl ring, which is unsubstituted or substituted with a methyl group;

n is an integer of from 1 to 2;

when n is 1, $R^3$ is an alkyl group of from one to twenty carbon atoms;

when n is 2, $R^3$ is an alkylene group of from two to eight carbon atoms; and

A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661, patented Nov. 18, 1975 disclose dicarboxylic acids and salts in which one carboxylic acid group is esterified with a 2,2,6,6-tetrasubstituted-4-hydroxy piperidine and having the formula:

[Structure diagram showing piperidine with CH₃ groups, R₃—N, R₁, R₂ substituents, and —O—C(O)—R₄—C(O)—O—M group, bracketed with subscript z]

wherein $R_1$ and $R_2$ independently of each other are straight-or branched-chain alkyl having from one to six carbon atoms, or together with the carbon to which they are bound form a cyclopentyl or cyclohexyl ring, which is unsubstituted or substituted with a methyl group;

$R_3$ is hydrogen, alkyl having from one to twelve carbon atoms, β-methoxyethyl, alkenyl having three or four carbon atoms, propargyl, benzyl or alkyl-sunbstituted benzyl;

$R_4$ is straight or branched-chain alkylene having five to eight carbon atoms, or the group $(CH_2)_mY(CH_2)_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al U.S. Pat. No. 3,939,163 patented Feb. 17, 1976 disclose closely similar compounds in which R₄ is alkylene having from one to four carbon atoms.

Randell et al U.S. Pat. No. 3,939,170 patented Feb. 17, 1976 disclose dehydropyridinyl sulfides, sulfoxides and sulfones having the formula:

[Structure diagram showing two dehydropyridinyl rings connected by X, with Y—N and N—Y¹ groups, and CH₃ substituents]

wherein

X is S, SO or SO₂ and Y and Y¹ are the same or different and each is H, OH, O- or a straight- or branched alkyl residue having from one to four carbon atoms, and salts thereof when Y and Y¹ are other than O-.

Randell et al in published patent application No. B408,123 published Apr. 13, 1976 disclose substituted piperidine-4-ols having the formula:

[Structure diagram showing piperidine-4-ol with H, OH, H₃C, H₃C, R₁, R₂ substituents and Y on N]

wherein $R_1$ and $R_2$ are the same or different and each is a straight- or branched alkyl residue having from one to twelve carbon atoms, or $R_1$ and $R_2$, together with the carbon atom to which they are attached, form a cycloalkyl residue having from five to twelve carbon atoms or the group:

$$\begin{array}{c} CH_3 \quad CH_3 \\ \diagup \\ \phantom{XXX} N-Y \\ \diagdown \\ R_1 \quad R_2 \end{array}$$

wherein

R$_1$ and R$_2$ have their previous significance and Y is a straight- or branched alkyl residue having from one to twenty carbon atoms, an alkenyl or alkynyl residue having from three to twenty carbon atoms, an aralkyl residue having from seven to twelve carbon atoms or the group —CH$_2$X wherein X is the group $$\begin{array}{cc} CH_2-CH- & \text{or} \quad -CH-OH \\ \diagdown\;\diagup & \phantom{XX} | \\ O & \phantom{XX} R_3 \end{array}$$

wherein

R$_3$ is hydrogen, a methyl or phenyl residue, the group $$\begin{array}{cc} -C-R_4 & \text{or} \quad -COR_4 \\ \| & \phantom{XX} \| \\ O & \phantom{XX} O \end{array}$$

wherein

R$_4$ is an alkyl residue having from one to twenty carbon atoms.

Cook U.S. Pat. No. 3,929,804 patented Dec. 30, 1975 discloses 4-piperidine acetamide compounds having the formula:

$$\left[ \begin{array}{c} R_3 \quad\quad CO-X \\ \diagdown\diagup \\ CH \\ | \\ H_3C \diagdown \phantom{X} \diagup R_1 \\ H_3C \diagup \phantom{X} \diagdown R_2 \\ \phantom{XX} N \\ \phantom{XX} | \\ \phantom{XX} H \end{array} \right]_n R_4 \quad\quad I$$

wherein

R$_1$ and R$_2$ are the same or different and each is a straight-or branched alkyl residue having from one to twelve carbon atoms, or R$_1$ and R$_2$, together with the carbon atom to which they are attached form a cycloalkyl group having from five to twelve carbon atoms;

R$_3$ is hydrogen, a straight-or branched alkyl residue having from one to four carbon atoms, an aralkyl residue having from seven to nine carbon atoms or a cycloalkyl group having from five or six carbon atoms;

R$_4$ is a metal ion or a hydrocarbyl residue having from two to twenty carbon atoms and being either unsubstituted or substituted by halogen or interrupted by one or more oxygen or sulphur atoms;

X is —O—, —S—, or >NR$_5$, wherein R$_5$ has the same significance as R$_3$; and n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group $$\begin{array}{c} R_7-CH-CH_2- \\ | \\ OH \end{array}$$

wherein

R$_7$ is hydrogen, alkyl or phenyl.

Randell et al U.S. Pat. No. 3,939,170, patented Feb. 17, 1976 provides di-4-(3,4-dehydro-2,2,6,6-tetramethyl piperidinyl) sulphides, sulphoxides and sulphones having the formula:

$$\begin{array}{ccc} CH_3 \; CH_3 & & CH_3 \; CH_3 \\ \diagdown\diagup & & \diagdown\diagup \\ Y-N \phantom{XX} -X- \phantom{XX} N-Y^1 & & \quad I \\ \diagup\diagdown & & \diagup\diagdown \\ CH_3 \; CH_3 & & CH_3 \; CH_3 \end{array}$$

wherein

X is S, SO or SO$_2$, and Y and Y$^1$ are the same or different and each is H, OH, 0° or a straight- or branched-alkyl residue having from one to four carbon atoms, and salts thereof when Y and Y$^1$ are other than 0°.

Preferably X is S.

Smith et al U.S. Pat. No. 3,954,779, patented May 4, 1976 provides 4-(4'-hydroxycyclohexyl)-2,2,6,6-tetramethyl piperidines and derivatives thereof having the formula:

$$\begin{array}{c} ZO \quad H \\ R_4 \diagdown \phantom{X} \diagup R_1 \\ H- \phantom{XXX} -H \\ R_3 \phantom{XXX} R_2 \\ H \diagup \phantom{X} \diagdown H \\ \phantom{XX} | \\ \phantom{XX} H \\ H_3C \diagdown \phantom{XX} \diagup CH_3 \\ H_3C \diagup \phantom{X} N \diagdown CH_3 \\ \phantom{XXX} | \\ \phantom{XXX} Y \end{array}$$

and salts thereof, wherein

R$_1$, R$_2$, R$_3$ and R$_4$ are the same or different and each is hydrogen, an alkyl residue having from one to nine carbon atoms, a cycloalkyl residue having from five to fourteen carbon atoms or a cycloalkyl-alkyl residue having from seven to fourteen carbon atoms;

Y is hydrogen;

O an alkyl residue having from one to four carbon atoms, or an aralkyl residue having from seven to twelve carbon atoms; and Z is hydrogen, an unsubstituted or substituted alkyl residue having from one to twenty carbon atoms, an alkenyl or alkynyl residue having from two to twenty carbon atoms, a cycloalkyl residue having from five to twelve carbon atoms, an aralkyl residue having from seven to twelve carbon atoms, an aryl residue having from six to twelve carbon atoms, or the group having the formula:

—COZ$_1$ wherein $Z_1$ has the same significance as Z as hereinbefore defined or $Z_1$ is a group $-NR_5R_6$
wherein
$R_5$ is hydrogen or an alkyl residue having from one to four carbon atoms and
$R_6$ is hydrogen, an alkyl residue having from one to twenty carbon atoms, a cycloalkyl residue having from five to twelve carbon atoms, an aralkyl residue having from seven to twelve carbon atoms or an aryl residue having from six to twelve carbon atoms.

Cook U.S. Pat. No. 3,959,291, patented May 25, 1976 provides derivatives of substituted 2-piperidinyl-4'-ethyl alcohol having the formula:

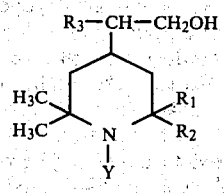

and salts thereof, wherein $R_1$ and $R_2$ are the same or different and each is an alkyl residue having from one to twelve carbon atoms, or $R_1$ and $R_2$, together with the carbon atom to which they are bound, form a cycloalkyl residue having from five to twelve carbon atoms in the ring;

Y is O, hydrogen, a straight- or branched-alkyl residue having from one to twenty carbon atoms, an alkenyl or alkynyl residue having from three to twelve carbon atoms, an aralkyl residue having from seven to twelve carbon atoms or a group having the formula:

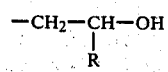

wherein

R is hydrogen, or a methyl or phenyl residue, and $R_3$ is hydrogen, or a straight- or branched-chain alkyl residue having from one to twelve carbon atoms.

Cook U.S. Pat. No. 3,971,795, patented July 27, 1976 provides N-substituted piperidinylidene derivatives having the formula:

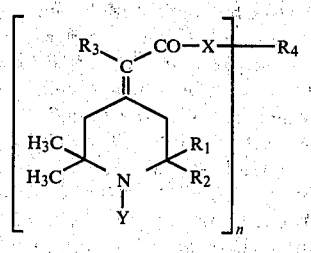

wherein n is 1, 2, 3 or 4,

Y is hydrogen or a straight- or branched-alkyl residue having from one to twelve carbon atoms, an alkenyl residue having from three to twelve carbon atoms or an aralkyl residue having from seven to twelve carbon atoms and $R_1$ and $R_2$ are the same or different and each is a straight- or branched-alkyl residue having from one to twelve carbon atoms, or $R_1$ and $R_2$ together with the carbon atom to which they are attached form a cycloalkyl group having from five to twelve carbon atoms;

$R_3$ is hydrogen, a straight- or branched-alkyl residue having from one to four carbon atoms, an aralkyl residue having from seven to twelve carbon atoms, a cycloalkyl group having five or six carbon atoms;

$R_4$ is a hydrocarbyl residue having from one to twenty carbon atoms being either unsubstituted or substituted by halogen, or interrupted by one or more oxygen or sulphur atoms or $R_4$ is a metal ion, or, when n is 1, $R_4$, in addition, is hydrogen or has the structure:

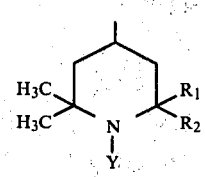

wherein

Y, $R_1$ and $R_2$ have their previous significance,

X is $-O-$, $-S-$ or $>NR_5$
wherein $R_5$ has the same significance as $R_3$ or when n is 1 in addition $R_5$ and $R_4$ together with the nitrogen atom to which they are bound form a heterocyclic residue having from four to ten carbon atoms; as well as salts of the amine function of the compound of formula I.

Murayama et al U.S. Pat. No. 3,975,357, patented Aug. 17, 1976 provides 1-substituted piperidine derivatives having the formula:

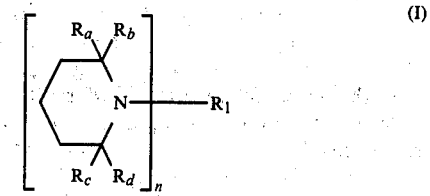

In the above formula, n represents 1 or 2.

$R_1$ represents when n=1, oxyl radical, hydroxy group, an alkyl group, a substituted alkyl group, an alkenyl group, an alkynyl group, an aralkyl group, a substituted aralkyl group or an acyl group, when n=2, an alkylene group (the alkylene chain may optionally be interrupted by an oxygen atom), 2-butenylene group, a group of the formula $-CH_2COO-R_7-O-COCH_2-$ wherein $R_7$ represents an alkylene group or xylylene group, or a group of the formula $-CH_2CH_2-OCO-R_8-_m COO-CH_2CH_2-$
wherein m represents 0 or 1, $R_8$ represents an alkylene group (the alkylene chain may optionally be interrupted by a sulfur atom), an alkenylene group, phenylene group or 1,4-cyclohexylene group.

$R_a$ and $R_b$ represent methyl group or $R_a$ and $R_b$ together with carbon atom to which they are attached, form cyclohexyl group.

$R_c$ represents methyl group.

$R_d$ represents an alkyl group having one to five carbon atoms.

$R_c$ and $R_d$ together with carbon atom to which they are attached, may form cyclopentyl group, cyclohexyl group, a group of the formula:

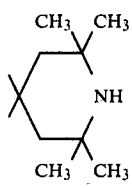

or a group of the formula

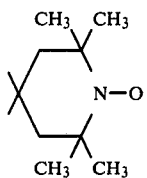

Murayama U.S. Pat. No. 3,975,462, patented Aug. 17, 1976 provides piperidine-spiro-hydantoin derivatives having the formula:

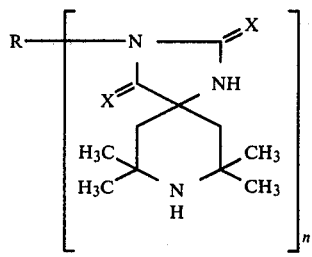

In the above formula (I), X represents oxygen atom or sulfur atom; n is an integer of 1 to 4 inclusive; and R represents when n is 1, an alkenyl group which may be substituted with halogen, an alkynyl group which may be substituted with phenyl, an aralkyl group which may be substituted with halogen, alkyl of one to four carbon atoms or halomethyl, a hydroxyalkyl group, an alkoxyalkyl group, an alkenyloxyalkyl group, an aryloxyalkyl group, an alkylthioalkyl group, an acyloxyalkyl group, an epoxyalkyl group, an N- alkyl-substituted aminoalkyl group, an alkoxycarbonyl alkyl group, an aryloxycarbonylalkyl group, an aliphatic acyl group, an alkoxycarbonyl group, a phosphino group which is substituted with phenoxy or alkoxy or a phosphinyl group which is substituted with phenoxy or alkoxy, when n is 2, an alkenylene group of four to eighteen carbon atoms, a dialkylene ether group, an aralkylene group, a bis-(acyloxyalkylene) group, or an alkylene-bis-(oxycarbonylalkyl) group, when n is 3, a tris-(acyloxyalkylene) group, an alkane-tris-(oxycarbonylalkyl) group or a group of the formula:

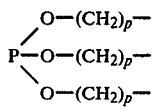

in which p is an integer of 1 to 8 inclusive and p's may be the same or different, and when n is 4, a tetrakis (acyloxyalkylene) group.

Avar et al U.S. Pat. No. 3,976,658, patented Aug. 24, 1976 provides pyrazole derivatives of the formula:

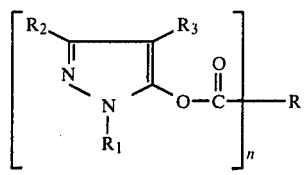

in which $R_1$ is a $C_{1-22}$ alkyl radical, a $C_{5-12}$ cycloalkyl radical, a $C_{6-12}$ cycloalkylalkyl radical, a $C_{7-12}$ aralkyl radical, of which the alkyl radical and the alkyl moiety of the cycloalkyl-alkyl radical are uninterrupted or interrupted by one or two sulphur atoms or by —COO—, and the aryl nucleus of the aralkyl radical is unsubstituted or substituted by a hydroxyl group and/or 1 or 2 $C_{1-12}$ alkyl radicals, or a phenyl group, unsubstituted or substituted by one or more substituents selected from one or two halogen atoms, a cyano group, a hydroxyl group, 1 or 2 $C_{1-12}$ alkyl radicals, 1 or 2 $C_{1-12}$ alkoxy radicals, a phenyl group and the radicals $R_4$—O— and $R_4$—$SO_2$—, wherein $R_4$ is a phenyl group, unsubstituted or substituted by 1 or 2 $C_{1-8}$ alkyl radicals, $R_2$, independently of $R_1$, has one of the significances of $R_1$, or is a cyano group or the radical —$COOR_5$, wherein $R_5$ is a $C_{1-12}$ alkyl radical, a $C_{5-12}$ cycloalkyl radical, a $C_{6-12}$ cycloalkyl-alkyl radical or a phenyl group, unsubstituted or substituted by a hydroxyl group and/or 1 or 2 $C_{1-8}$ alkyl radicals.

$R_3$ is a hydrogen atom or one of the significances of $R_1$, —$COR_1$ or —$COOR_5$, n is 1, 2 or 3, and R, when n is 1, is a phenyl group unsubstituted or substituted by a total of up to 3 substituents selected from one hydroxyl group, one to three halogen atoms, one phenyl group, one benzyl group, one phenoxy group, one to three alkyl radicals each containing one to eight carbon atoms and the sum of the carbon atoms not exceeding twelve, and one to three alkoxy radicals each containing one to twenty-two carbon atoms and the sum of the carbon atoms not exceeding twenty-two, or a monovalent naphthalene radical, or a monovalent radical of thiophene, benzothiophene, dibenzothiophene, furan, benzofuran, or dibenzofuran, and when n is 2, is a phenylene group, unsubstituted or substituted by a $C_{1-4}$ alkyl radical and/or a halogen atom, or a divalent naphthalene radical, or a divalent radical of thiophene or dibenzofuran, and when n is 3, is a 1,3,5-trivalent benzene radical.

Murayama et al, U.S. Pat. No. 4,061,616 patented Dec. 6, 1977, provides piperidyl derivatives having the following formula (I) or an acid addition salt thereof:

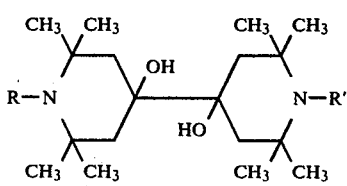

wherein

R and R', which may be the same or different, and each represents hydrogen atom, an alkyl group, an alkenyl group, an alkynyl group, an aralkyl group, a hydroxyalkyl group, an alkoxyalkyl group, an aliphatic or aromatic acyloxyalkyl group, a cyanoalkyl group, a halogenoalkyl group, an epoxyalkyl group, an alkoxycarbonylalkyl group, an aliphatic acyl group, an alkoxycarbonyl group or an aralkoxycarbonyl group.

Hillard et al U.S. Pat. No. 4,064,102 discloses 2,2,6,6-tetramethylpiperidine-4-carboxylic acid ester compounds having the formula:

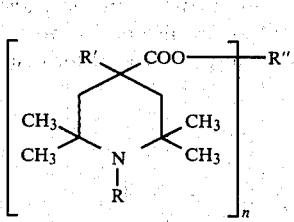

where

R is hydrogen or alkyl (C$_1$-C$_8$); R' is hydrogen, hydroxyl or alkoxy (C$_1$-C$_8$); R" is alkyl (C$_1$-C$_{20}$), alkylene (C$_2$-C$_{12}$), cycloalkyl, wherein the cycloaliphatic ring contains 5- or 6-carbon atoms, cycloalkylene, wherein the cycloaliphatic ring may contain lower alkyl substituents, arylene, aralkylene and alkenyl (C$_3$-C$_{20}$); n is an integer from 1 to 4.

Murayama U.S. Pat. No. 4,066,615, patented Jan. 3, 1978, provides stabilizers having the formula:

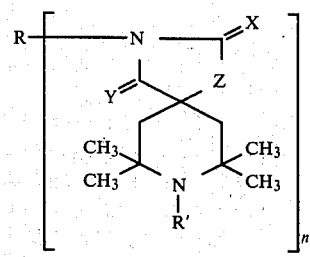

wherein:

R' represents an alkyl, an acyl, an alkoxycarbonyl, an amino or nitroso group;

X represents oxygen or sulfur;

Y represents oxygen, sulfur or a group of the formula =N—R" in which R" is hydrogen or alkyl;

Z represents oxygen or a group of the formula >N—R''' in which R''' is hydrogen or alkyl;

n is an integer of 1 to 4; and

R represents, when n is 1, alkyl, aryl, cycloalkyl, alkoxycarbonyl, substituted phosphino or substituted phosphinyl, when n is 2, alkylene, alkenylene, arylene, aralkylene; alkylenediphenylene, bis-(carboxycarbonyl) alkylene, alkylene-bis-(oxycarbonylalkyl), dialkylene ether or diphenylene ether, when n is 3, alkanetriyl, tris-(alkoxycarbonyl) alkanetriyl, alkanetriyl-tris-(oxycarbonylalkyl) or a group of the formula

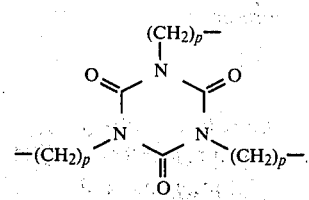

in which p is an integer of 1 through 8 inclusive, and, when n is 4, alkanetetrayl, tetrakis-(alkoxycarbonyl) alkanetetrayl or alkanetetrayl-tetrakis-(oxycarbonylalkyl).

Soma et al U.S. Pat. No. 4,097,587 patented June 27, 1978 provides 7,7,9,9-tetra-substituted-1,3,8-triazaspiro [4.5] decane-2,4-diones having an alkyl or allyl group at either the 6- or the 10- position which are said to be useful for the stabilization of polymers against photo- and thermal-deterioration.

These compounds have the formula:

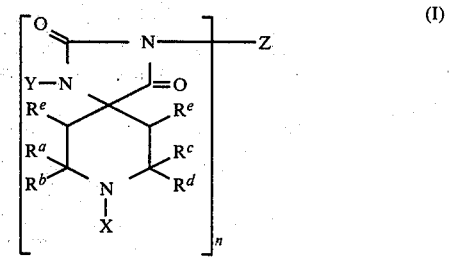

wherein:

R$^a$ represents a methyl group;

R$^b$ represents a lower alkyl group;

R$^c$ represents an alkyl group;

R$^d$ represents an alkyl group, a phenyl group or an aralkyl group; or

R$^c$ and R$^d$, together with the carbon atom to which they are attached, represent a cycloalkyl group;

one of R$^e$ and R$^{e'}$ represents a hydrogen atom and the other of R$^e$ and R$^{e'}$ represents a lower alkyl group or an allyl group;

n is 1 or 2;

Y represents a hydrogen atom or, when neither X nor Z represents a hydrogen atom, Y represents a hydrogen atom, a methyl group, an ethyl group, an allyl group or a benzyl group;

X represents a hydrogen atom, an oxyl radical, a lower alkyl group, an alkenyl group, a benzyl group, a 2,3-epoxypropyl group or a group of formula —CH$_2$CH$_2$OR$^1$ (wherein R$^1$ represents a hydrogen atom or an aliphatic, aromatic, araliphatic or alicyclic acyl group);

when n=1:

Z represents a hydrogen atom, an alkyl group, an alkenyl group, an aralkyl group which is unsubstituted or has one or more substituents in its aryl moiety, an aryl group which is unsubstituted or has one or more chlorine and/or methyl substituents, a cyclohexyl group, a 2,3-epoxypropyl group, an alkoxyalkyl group, a phenoxyalkyl group, a group of formula —CH$_2$COOR$^2$ (wherein R$^2$ represents an alkyl group or a phenyl group) or a group of formula

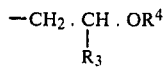

(wherein R³ represents a hydrogen atom, a methyl group or a phenyl group, and R⁴ represents a hydrogen atom or an aliphatic aromatic, araliphatic or alicyclic acyl group);

when n=2:

Z represents an alkylene group, which is optionally interrupted by an oxygen atom, a 2-butenylene group, a xylylene group; an arylene group which is unsubstituted or has one or more methyl substituents, a group of formula

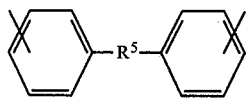

(wherein R⁵ represents an oxygen atom or a methylene group), a group of formula —CH₂.COOR⁶OCO.CH₂— (wherein R⁶ represents an alkylene group) or a group of formula

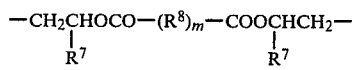

(wherein R⁷ represents a hydrogen atom, a methyl group or a phenyl group, m is 0 or 1 and R⁸ represents an alkylene group optionally interrupted by a sulphur atom, an alkenylene group, a phenylene group or a 1,4-cyclohexylene group); and acid addition salts thereof.

Mayer et al U.S. Pat. No. 4,097,452 patented June 27, 1978 provides diazadispiro-hexadecane compounds having the formula:

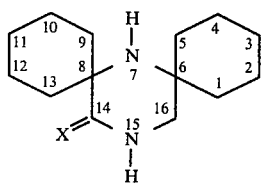

wherein X means =O, =NH or

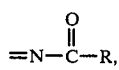

R being an alkyl group with one to seventeen carbon atoms, preferably the methyl group, for the stabilization of organic matter against the decomposition by light and heat.

Matsui et al Japanese Pat. No. 73-3211 discloses 2,2,6,6-tetramethyl-4-amino piperidine compounds.

Murayama et al Japanese Pat. No. 68-22653 discloses the compound

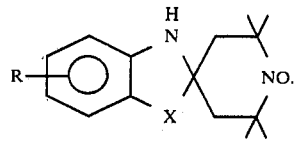

in which

X represents NH, oxygen or sulfur; and
R represents alkyl, benzyl or phenyl.

In accordance with the instant invention, 2,2,6,6-tetramethyl-4-piperidyl carboxylic acid esters and amides of mono and poly alcohols, phenols and amides are provided, useful as stabilizers for organic polymeric materials, and having the general formula:

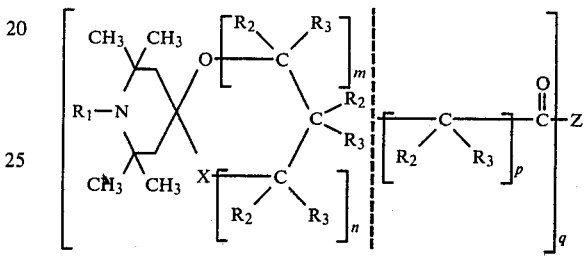

wherein:

$R_1$, $R_2$ and $R_3$ are selected from the group consisting of hydrogen and alkyl having from one to about eighteen carbon atoms;

X is oxygen or imino $>$NH;

m is zero, 1 or 2;

n is zero, 1 or 2;

m+n is 1 or 2;

p is zero or 1;

q is 1 to 6;

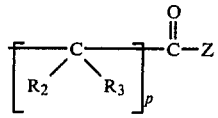

is linked to carbon in place of one $R_2$ or $R_3$ group; and Z is selected from the group consisting of:

(a) OR₅ where R₅ is alkyl, aryl or cycloalkyl having one to twenty-four carbon atoms and hydroxy-, carboxy- and oxy-substituted such groups having from one to five OH or O groups; and 2,2,6,6-tetramethyl-4-piperidyl;

(b) OR₆O where R₆ is alkylene, arylene or cycloalkylene having one to twenty-four carbon atoms and hydroxy-substituted such groups having one to four OH groups;

R₆ alkylene, arylene or cycloalkylene can include oxyether —O— and thioether —S— linking groups attached to alkylene, arylene or cycloalkylene groups as in polyoxyalkylene and polythioalkylene groups and polyoxyalkylene arylene groups having from one to about five oxy or thio groups and from two to about six alkylene groups having from two to about six carbon atoms;

(c)

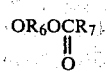

where $R_6$ is alkylene, arylene or cycloalkylene having one to twenty-four carbon atoms and hydroxy-substituted such groups having one to four OH groups;

$R_6$ alkylene, arylene or cycloalkylene can include oxyether —O— and thioether —S— linking groups attached to alkylene, arylene or cycloalkylene groups as in polyoxyalkylene and polythioalkylene groups and polyoxyalkylene arylene groups having from one to about five oxy or thio groups and from two to about six alkylene groups having from two to about six carbon atoms;

$R_7$ is alkyl, aryl or cycloalkyl having one to twenty-four carbon atoms and hydroxy-substituted such groups having from one to five OH groups;

(d) $NHR_5$ where $R_5$ is alkyl, aryl or cycloalkyl having one to twenty-four carbon atoms and amino-substituted such groups having from one to five amino groups;

(e)

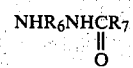

where $R_6$ is alkylene, arylene or cycloalkylene having one to twenty-four carbon atoms and amino-substituted such groups having one to four amino groups;

$R_7$ is alkyl, aryl or cycloalkyl having one to twenty-four carbon atoms and amino-substituted such groups having one to five amino groups;

(f) $—NHNH_2$; $—NHNH—$; $—NHNHCOCONHNH_2$; $NHNHCOR_7$; $—NHNHCOR_6—CONHNH_2$; $—NHNHCOR_6CONHNH—$; $—NHNHCOCONHNH—$; $—NHR_6NH_2—$; $—NHR_6NH—$; $NHR_6NHCOR_6CONHR_6NH$;

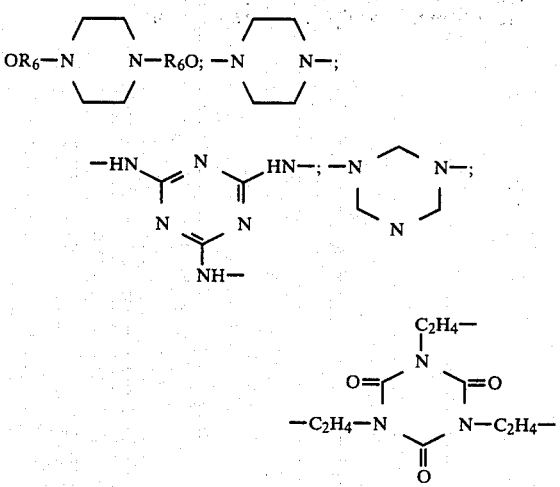

where $R_6$ is alkylene, arylene or cycloalkylene having one to twenty-four carbon atoms and amino-substituted such groups having one to four amino groups; and such groups including oxyether and thioether linking groups as in (b) above, and $R_7$ is as in (c) above.

The $R_1$, $R_2$ and $R_3$ alkyl have from one to about eighteen carbon atoms. Exemplary are methyl, ethyl, n-propyl, isopropyl, n-butyl, isobutyl, tertiary-butyl, secondary butyl, n-amyl, isoamyl, tertiary-amyl, n-hexyl, isohexyl, secondary hexyl and tertiary-hexyl, heptyl, octyl, isooctyl, 2-ethyl hexyl, nonyl, isononyl, decyl, undecyl, dodecyl, tridecyl, tetradecyl, hexadecyl and octadecyl.

The Z radical has from two to about twenty-four carbon atoms in an open chain or cyclic saturated or ethylenically unsaturated or aromatic structure, or mixed open chain substituted cyclic saturated or ethylenically unsaturated or aromatic structure.

Exemplary $R_5$ and $R_7$ alkyl include those mentioned above for $R_1$, $R_2$ and $R_3$ and in addition eicosyl and behenyl.

Exemplary $R_5$ and $R_7$ cycloalkyl and aryl include phenyl, benzyl, cyclohexyl, cyclopentyl, cycloheptyl, ethyl benzyl, phenethyl, phenmethyl, naphthyl, and phenanthryl.

Exemplary $R_6$ alkylene, cycloalkylene and arylene include ethylene, propylene, butylene, pentylene, hexylene, octylene, nonylene, decylene, dodecylene, tetradecylene, hexadecylene, octadecylene, cyclopentylene, cyclohexylene, cycloheptylene, ethylidene, 2,2,6,6-tetraethylene cyclohexylene, 1-hydroxyl-2,2,6,6-tetraethylene cyclohexylene; $R_6$ and $R_7$ alkylene can include oxyether —O— and thioether —S— linking groups between alkylene groups as in polyoxyalkylene and polythioalkylene groups and polyoxyalkylene arylene groups having from one to about five oxy or thio groups and from two to about six alkylene groups having from two to about six carbon atoms.

The Z arylene and cycloalkylene have from six to twenty-four carbon atoms and include phenylene, naphthylene and phenanthrylene; methylcyclohexylene, dibutyl cyclohexylene, ethyl cyclopentylene, trimethyl cyclobutylene, cyclopentane dimethylene; cycloheptane dimethylene; cyclohexane dimethylene; cyclohexane dipropylene; cyclopentane diethylene; and cyclohexane dibutylene; benzene dimethylene; xylene; 2,2-diphenyl isopropylidene; phenethylene, ethylphenylene, propylphenylene, butylphenylene, tolylene, phenpropylene, phenbutylene, naphthethylene and ethylnaphthylene.

Exemplary $R_5$ and $R_7$ amino and hydroxy-substituted alkyl, cycloalkyl and aryl include amino ethyl, hydroxyethyl, aminopropyl, hydroxypropyl, aminobutyl, hydroxybutyl, aminohexyl, hydroxyhexyl, hydroxyoctyl, hydroxydodecyl, hydroxyoctadecyl, aminooctyl, aminododecyl, aminooctadecyl, aminobehenyl, hydroxybehenyl, hydroxycyclohexyl, hydroxycyclopentyl, hydroxycycloheptyl, hydroxyphenyl, hydroxynaphthyl, hydroxyphenanthrene, aminocyclohexyl, aminocyclopentyl, aminocycloheptyl, aminophenyl, aminonaphthyl, aminophenanthryl, and such radicals containing from two to five amino and/or hydroxyl groups.

Exemplary $R_6$ amino and hydroxy-substituted alkylene, cycloalkylene and arylene include aminopropylene, hydroxypropylene, aminobutylene, hydroxybutylene, diethyleneamine, triethylenediamine, tetrahydroxyhexylene, trihydroxypentylene, dihydroxybutylene, diaminobutylene, aminophenylene, aminonaphthylene, aminophenanthrene, aminocyclohexylene, aminocyclopentylene, aminocycloheptylene, and such radicals containing from two to five amino and/or hydroxy groups.

It will be apparent that the Z, $R_5$, $R_6$ and $R_7$ groups are derived from the corresponding mono and polyhydric alcohols, phenols and amines.

Exemplary monohydric alcohols and phenols are methanol, ethanol, propanol, butanol, 2,2,6,6-tetramethyl-4-piperidinol, octanol, 2-ethylhexanol, decanol, dodecanol, tridecanol, tetradecanol, octadecanol, cyclohexanol, cyclopentanol, cycloheptanol, phenol, cresol, xylenol, phenylphenol, cyclohexylphenol, t-butylphenol, di-t-butylphenol, styrenated phenol, octylphenol, nonylphenol, di-nonylphenol, and dodecylphenol.

Exemplary dihydric and higher polyhydric alcohols and phenols include ethylene glycol, diethylene glycol, triethylene glycol, 1,3-propanediol, 1,2-propanediol, 1,4-butanediol, 1,2-butanediol, 1,6-hexanediol, 1,10-decanediol, 1,4-cyclohexanedimethanol, 1,4-benzenedimethanol, pentanediol, hexanediol, neopentylglycol, thiodiethylene glycol, glycerol, erythritol, trimethylolethane, trimethylolpropane, tris(2-hydroxyethyl)isocyanurate, diglycerine, ditrimethylolpropane, pentaerythritol, xylitol, tetramethylolcyclohexanol, dipentaerythritol, sorbitol, mannitol, inositol, cyclohexane, dimethanol, phenyldimethanol, hydrogenated Bisphenol A, catechol, t-butylcatechol, resorcinol, hydroquinone, Bisphenol A, 4,4′-thiobisphenol, 4,4′-methylenebisphenol, 4,4′-sulfobisphenol, 2,2′-thiobisphenol, 4,4′-cyclohexylidenebisphenol, 2,2′-thiobis (4-t-octylphenol), 4,4′-butylidenebis (2-t-butyl-5-methylphenol), 4,4′-thiobis (2-t-butyl-5-methylphenol) and 1,1,3-tris (2-methyl-4-hydroxy-5-t-butylphenyl)butane, cyclohexanediol hydroquinone, 2,5-di-t-butylhydroquinone, cyclohexanediol hydroquinone, 2,5-di-t-butylhydroquinone, 2,3,6-trimethylhydroquinone, 2-methylresorcinol; 2,6-di-t-butylresorcinol; 2,2′-methylene-bis-(4-methyl-6-t-butylphenol); 2,2′-methylene-bis-(4-methyl-6-(α-methylcyclohexyl)phenol); 2,2′-n-butylidene-bis-(4,6-di-methylphenol), bis-1,1-(2′hydroxy-3′,5′-dimethylphenyl)-3,5,5-trimethylhexane; 2,2′-cyclohexylidene bis-(4-ethyl-6-t-butylphenol); 2,2′-isopropylbenzylidene-bis-(4-ethyl-6-t-butylphenol); 2,2′-thio-bis-(4-t-butyl-6-methylphenol); 2,2′-thio-bis-(4-methyl-6-t-butylphenol); 2,2′-thio-bis-(4,6-di-t-butylphenol); 2,2′-thio-bis-(4,6-di-butylphenol); 4,4′-bis-(2,6-di-t-butylphenol); 4,4′-bis-(2,6-di-t-butylphenol); 4,4′-methylene-bis-(2-methyl-6-t-butylphenol); 4,4′-methylene-bis-(2,6-di-t-butylphenol); Bisphenol A, 4,4′-isopropylidene-bis-(2-phenylethylphenol); 4,4′-n-butylidene-bis-(3-methyl-6-t-butylphenol); 4,4′-cyclohexylidene-bis-(2-t-butylphenol); 4,4′-cyclohexylidene-bis-(2-cyclohexylphenol); 4,4′-benzylidene-bis-(2-t-butyl-5-methylphenol); 4,4′-oxo-bis-(3-methyl-6-isopropylphenol); 4,4′-thio-bis-(3-methyl-6-t-butylphenol); 4,4′-sulfo-bis-(3-methyl-6-t-butylphenol); and bis-(2-methyl-4-hydroxy-5-t-butylbenzyl) sulfide.

Exemplary mono and poly amines include ammonia, hydrazine, diethylamine, butylamine, octylamine, aniline, methylenediamine, ethylenediamine, propylenediamine, hexamethylenediamine, octamethylenediamine, dodecanediamine, 1,3-bis(aminomethyl) cyclohexane, morpholine, piperidine, phenylene diamine, 2,2,6,6-tetramethyl-4-aminopiperidine, piperazine, guanidine, melamine, hexahydro-s-triazine, diethylenetriamine, triethylenetetramine and 1,3,6-hexanetriyl-2,2′,2″-tris-(4,6-diamino-1,3,5-triazine).

Exemplary carboxylic acids esterifying polyhydric alcohols or amidifying polyamines include formic acid, acetic acid, propionic acid, octanoic acid, lauric acid, stearic acid, acrylic acid, crotonic acid, oleic acid, glycolic acid, dodecylthiopropionic acid, phenylacetic acid, cinnamic acid, 3,5-di-t-butyl-4-hydroxyphenylpropionic acid, benzoic acid, salicylic acid, toluic acid, t-butylbenzoic acid, 3,5-di-t-butyl-4-hydroxybenzoic acid, oxalic acid, malonic acid, succinic acid, glutaric acid, adipic acid, sebacic acid, azelaic acid, dodecanedicarboxylic acid, hexadecanedicarboxylic acid, eicosane dicarboxylic acid, maleic acid, tartaric acid, malic acid, diglycolic acid, thiodipropionic acid, phthalic acid, isophthalic acid, terephthalic acid, butanetricarboxylic acid, butenetricarboxylic acid, trimellitic acid, trimesic acid, butane tetracarboxylic acid, propanetetracarboxylic acid, pyromellitic acid, benzophenonetetracarboxylic acid, tetrahydrophthalic acid, endomethylenetetrahydrophthalic acid, pyrollidonecarboxylic acid, nicotinic acid, citric acid, N,N′-dicarboxyethylpiperidine and 3,4-dihydroxythiophenedicarboxylic acid.

The following compounds are exemplary:

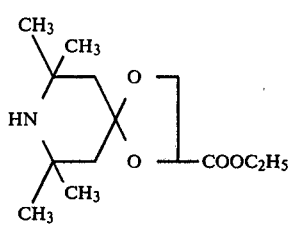

1.

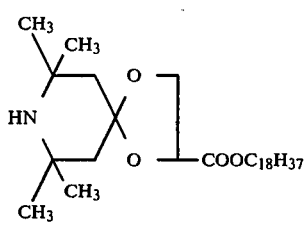

2.

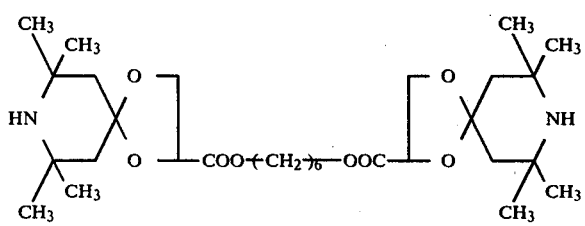

3.

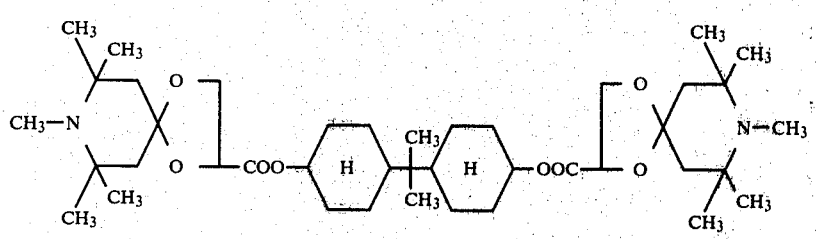
4.
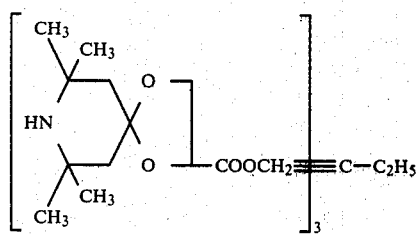
5.
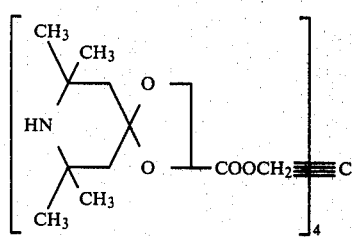
6.
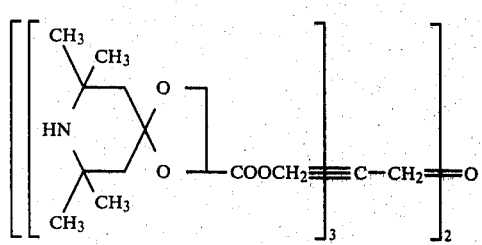
7.
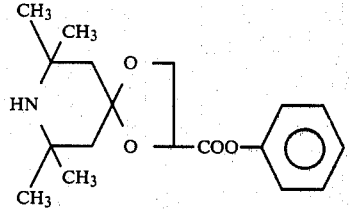
8.
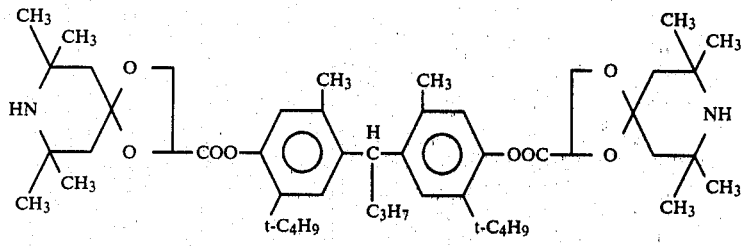
9.

10.
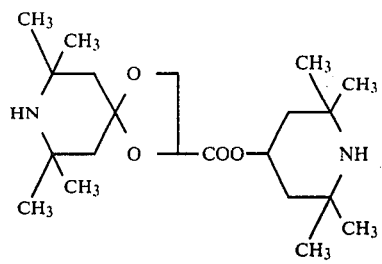
11.
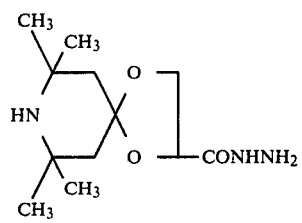
12.
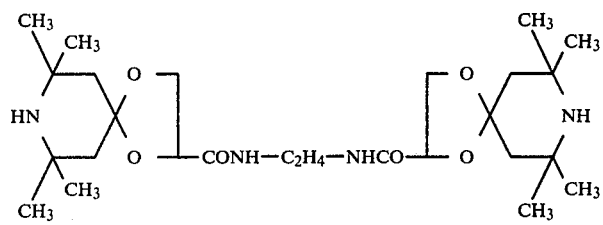
13.
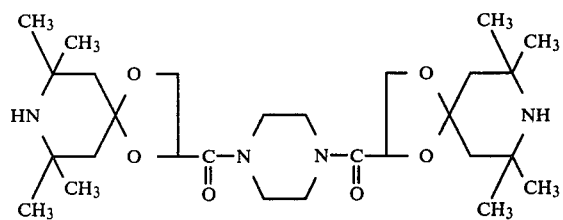
14.
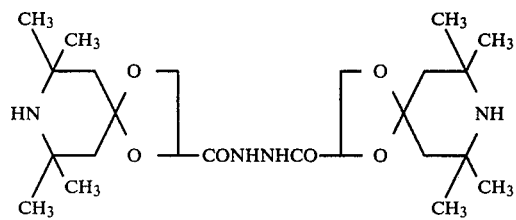
15.
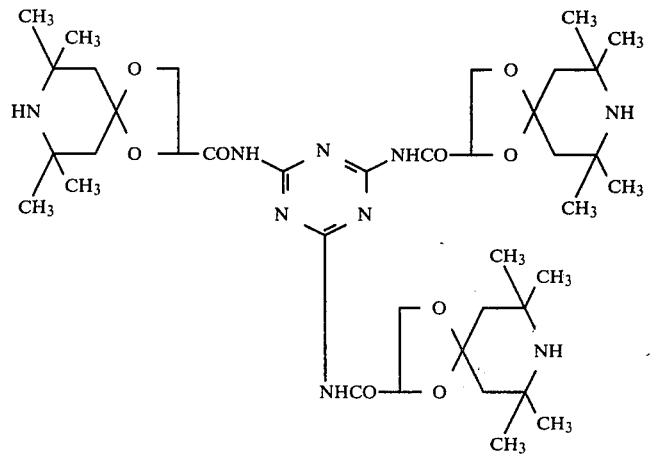

-continued
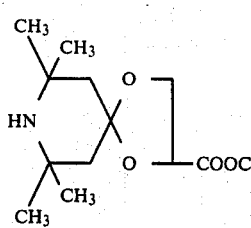—COOC₂H₄OOC—⟨phenyl⟩—COOC₂H₄OOC—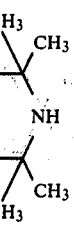 16.
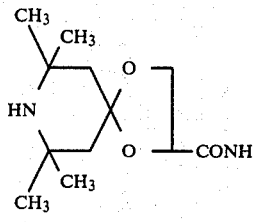—CONHNHCOCONHNHCO—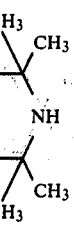 17.
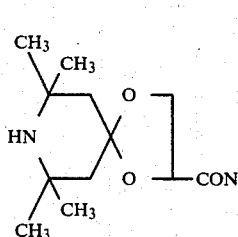—CONHNHCO—C₄H₈—CONHNHCO—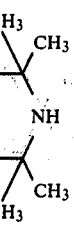 18.
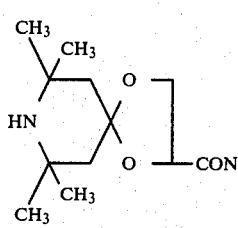—CONHNHCO—⟨phenyl-OH⟩ 19.
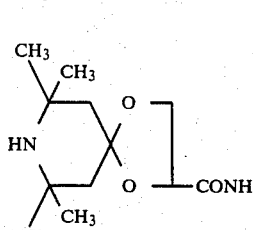—CONHNHCOC₂H₄—⟨3,5-di-t-C₄H₉-4-OH-phenyl⟩ 20.
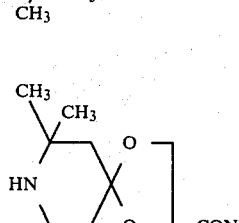—CONHNHCO—⟨cyclohexyl⟩—COOCH₃ 21.
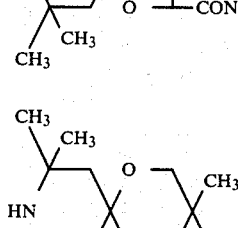—C(CH₃)(COOC₁₂H₂₅)— 22.

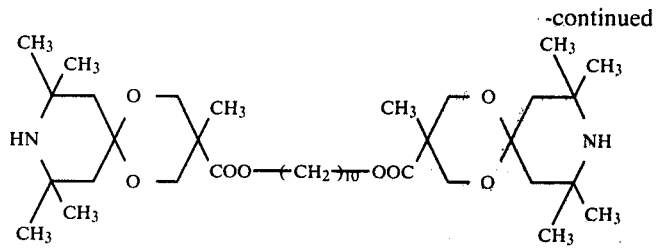 23.
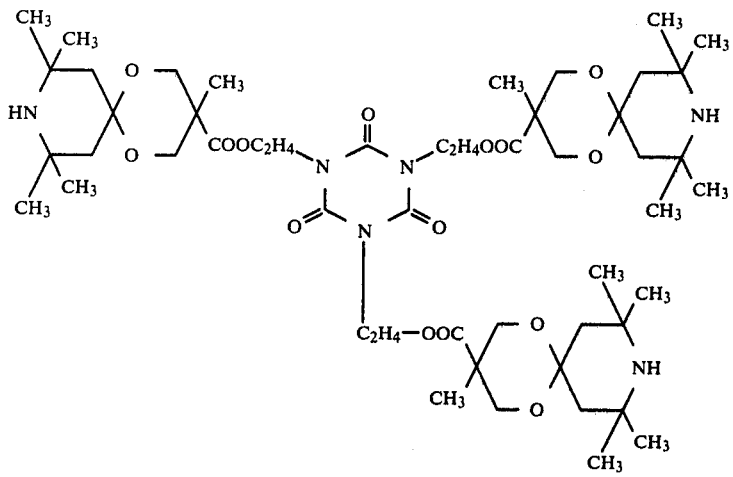 24.
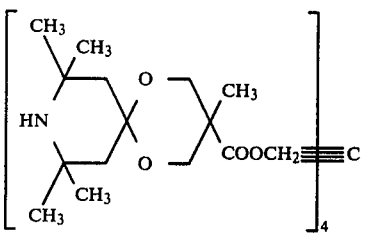 25.
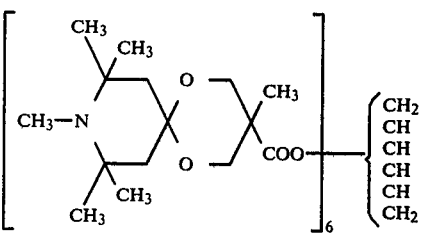 26.
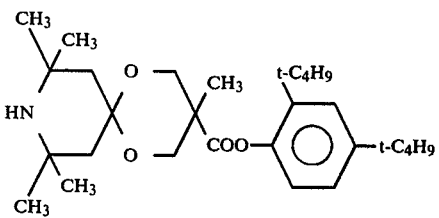 27.
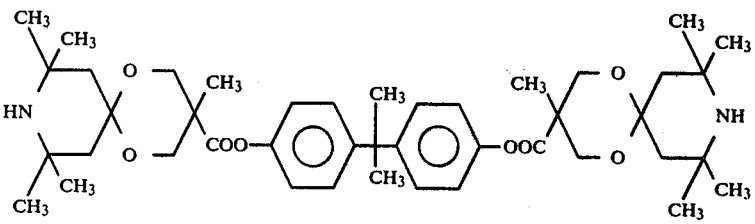 28.

-continued
29.
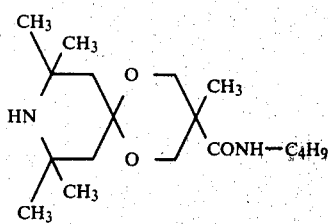
30.
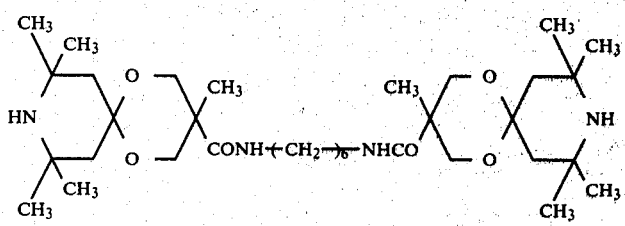
31.
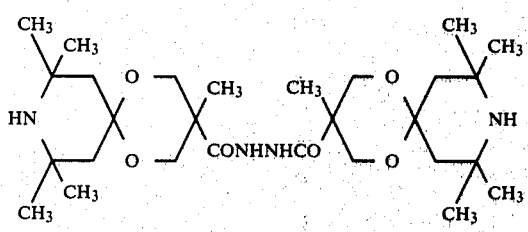
32.
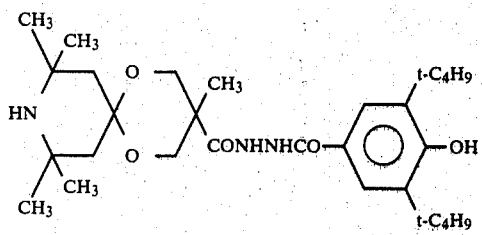
33.
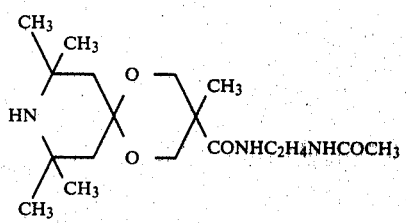
34.
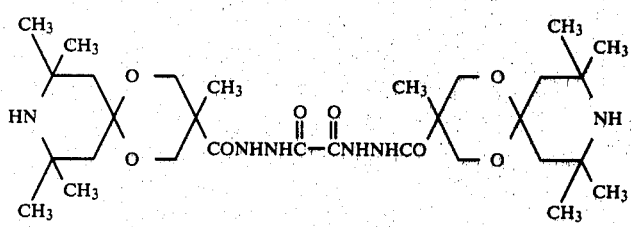
35.
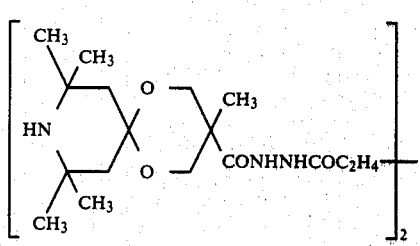

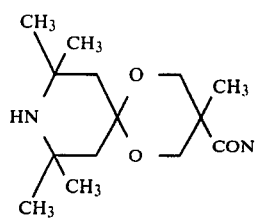 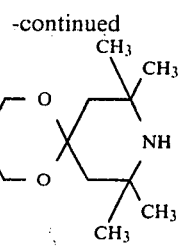 36.
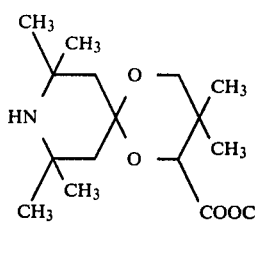 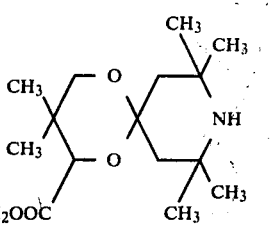 37.
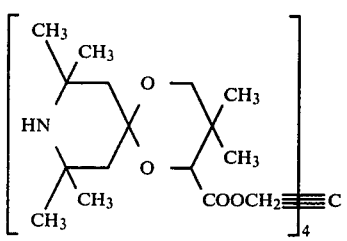 38.
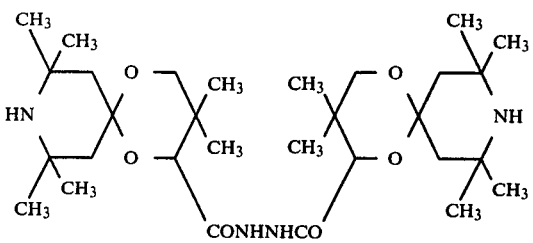 39.
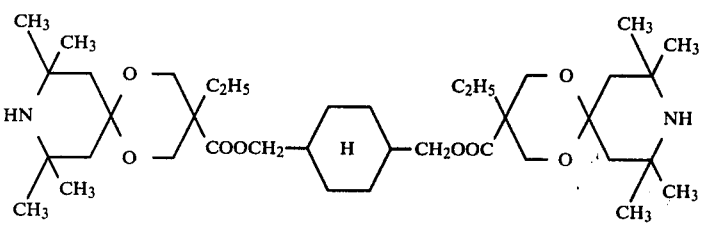 40.
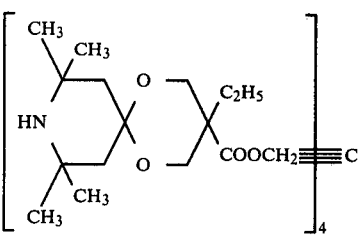 41.
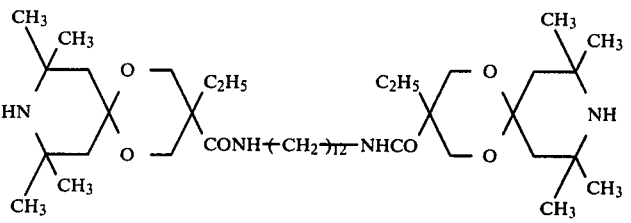 42.

-continued
43.
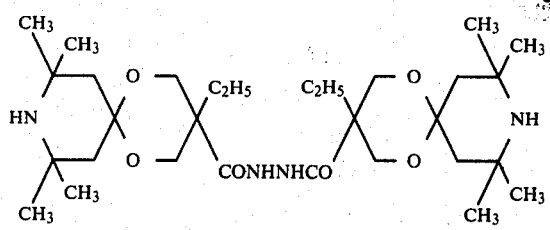
44.
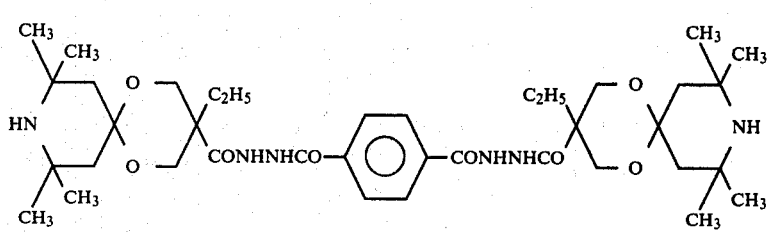
45.
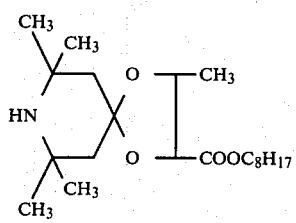
46.
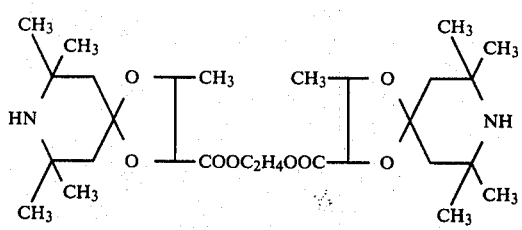
47.
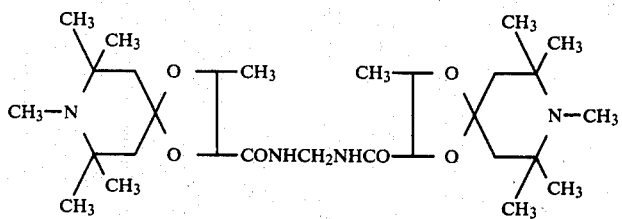
48.
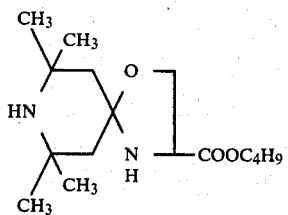
49.
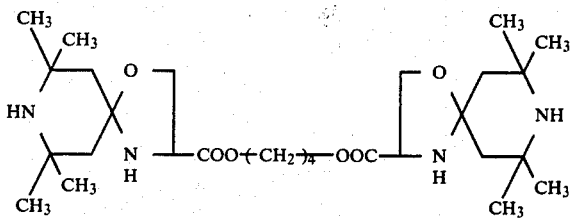

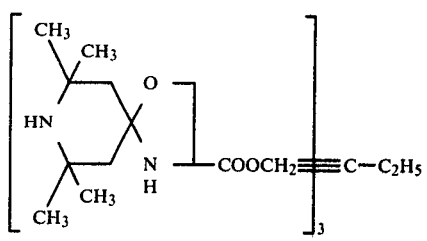 50.
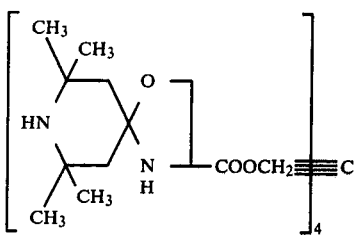 51.
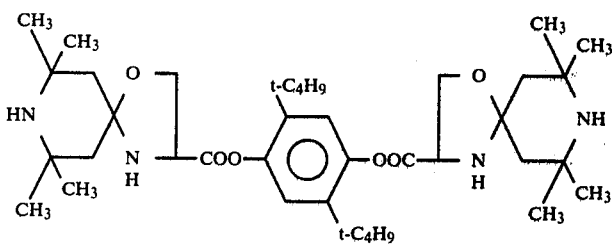 52.
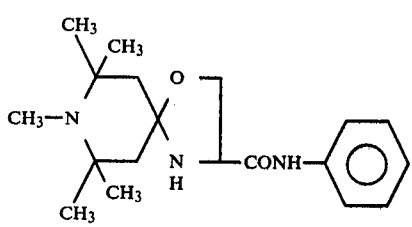 53.
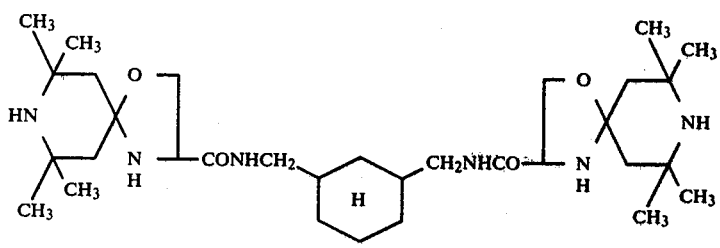 54.
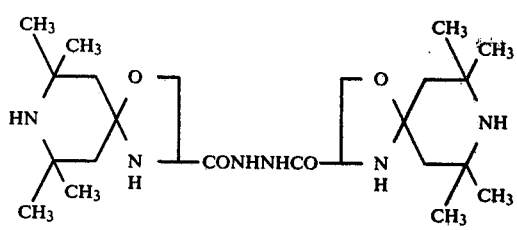 55.

56.
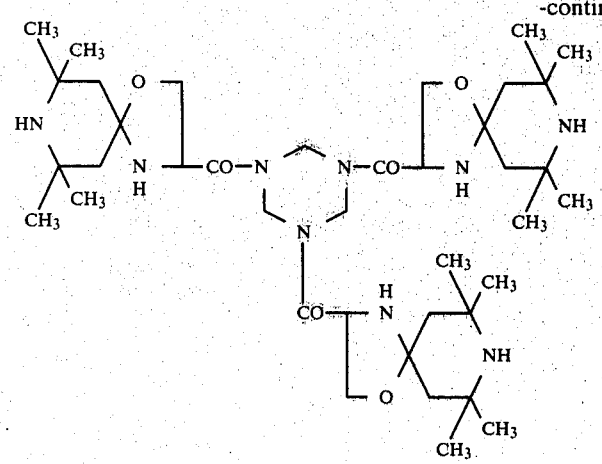
57.
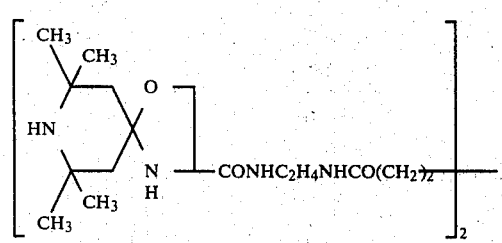
58.
59.
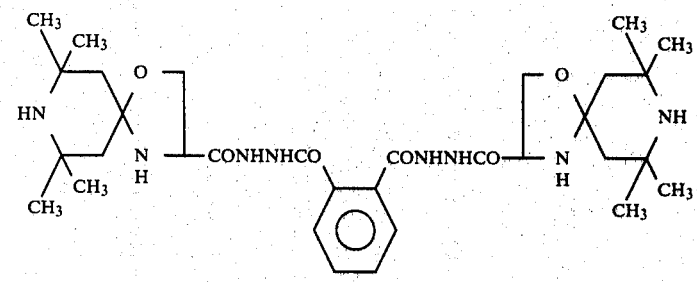
60.
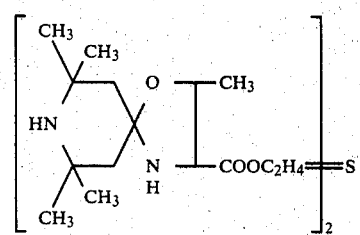
61.
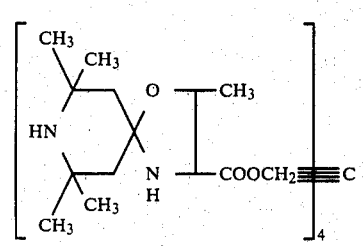

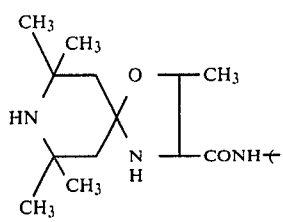 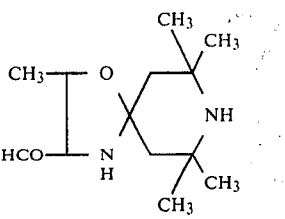 62.
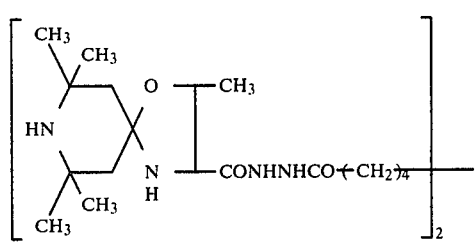 63.
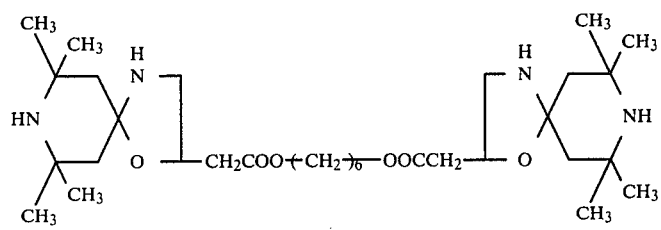 64.
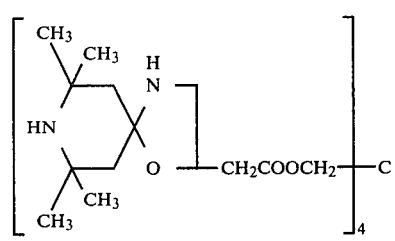 65.
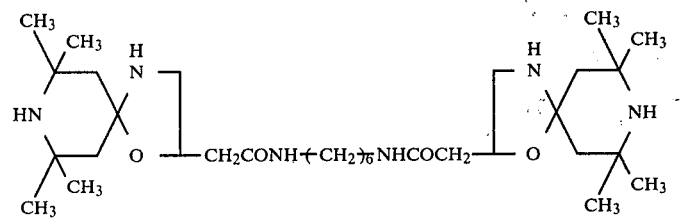 66.
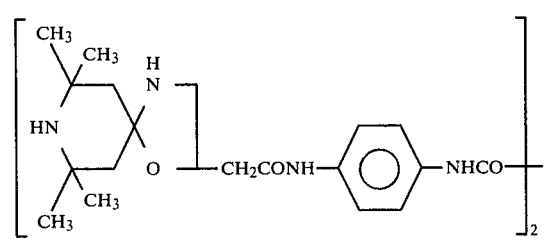 67.
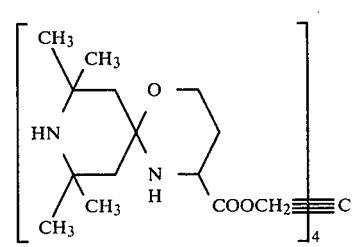 68.

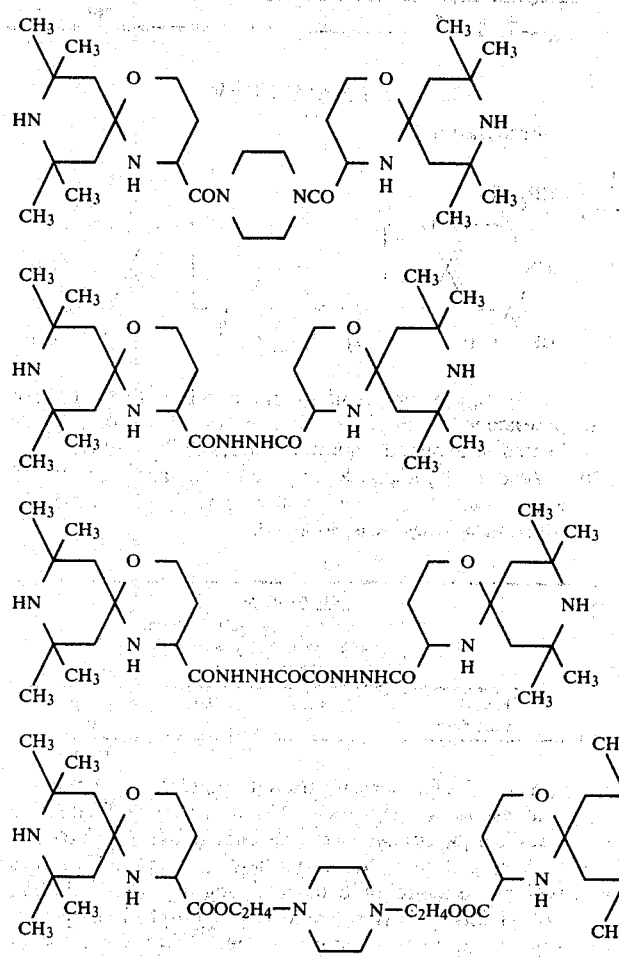

The compounds in accordance with the invention are readily prepared using conventional procedures. The starting materials are either available or readily synthesized without difficulty. The corresponding 2,2,6,6-tetrasubstituted-4-piperidone

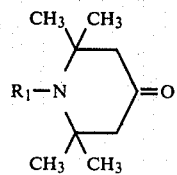

or dialkyl ketal thereof is used as a starting material for the 2,2,6,6-tetrasubstituted-4-piperidyl group. This is reacted optionally in the presence of an organic solvent with the corresponding carboxylic acid and then with the corresponding alcohol, phenol or amine. Any alkaline catalyst conventionally employed for esterification reactions can be used, as an alkali or alkaline earth metal oxide or hydroxide or an alkaline salt of an alkali or alkaline earth metal, such as carbonate, or hydride, or alcoholate. Sodium is quite satisfactory, and so are sodium hydroxide, lithium carbonate, sodium carbonate, potassium carbonate, lithium hydroxide, potassium hydroxide, sodium hydride, lithium hydride, potassium hydride, calcium hydride, the oxides and hydroxides of calcium, strontium and barium, and the alcoholates, usually of methyl, ethyl or isopropyl alcohol, or phenolates of all of these metals. The oxy group of the piperidine becomes replaced with the carboxylic acid group, and free carboxylic acid groups become esterified with the hydroxy group of the alcohol or phenol forming the 4-piperidinyl carboxylic acid ester. In the case of the amine, an amide group or groups are formed.

The following Examples are illustrative of the preparation.

EXAMPLE I

Preparation of

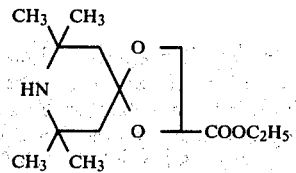

22.0 g glyceric acid ethyl ester, 50.6 g 4,4-dimethoxy-2,2,6,6-tetramethylpiperidine hydrochloride, and 0.5 g of p-toluenesulfonic acid were dispersed in 100 ml of benzene.

The whole was heated and stirred for seven hours at temperatures up to 80° C., while distilling off the methanol as it was liberated. After cooling, the solution was washed with 20% aqueous KOH solution, and then with water. The solution was distilled, and 38.5 g of the portion of boiling range 112° to 117° C./2 mm Hg was collected.

IR Analysis:
$\nu_{C=O}$: 1760 cm$^{-1}$, $\nu_{NH}$: 3320 cm$^{-1}$
$\nu_{C-O}$(ketal): 1120 cm$^{-1}$
Elemental Analysis:

|  | C % | H % | N % |
|---|---|---|---|
| Found | 61.6 | 9.27 | 5.14 |
| Calculated | 62.0 | 9.23 | 5.17 |

EXAMPLE II

Preparation of

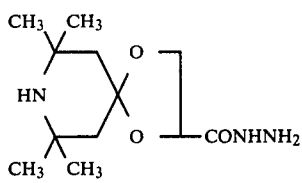
CONHNH$_2$ 10.8 g of the compound of Example I, ethyl 7,7,9,9-tetramethyl-1,4-dioxa-8-aza-spiro[4,5]-decane-2-carboxylate, 4.0 g of 80% hydrazine hydrate and 10 ml of ethanol were heated and stirred for eight hours under reflux.

After cooling, white crystals precipitated and were filtered and dried. 9.8 g of white crystals, m.p. 107° to 109° C. was obtained.

IR Analysis:
$\nu_{C=O}$: 1650 cm$^{-1}$, $\nu_{NH}$: 3210 cm$^{-1}$ and 3300 cm$^{-1}$
$\nu_{C-O}$(ketal): 1100 cm$^{-1}$
Elemental Analysis:

|  | C % | H % | N % |
|---|---|---|---|
| Found | 56.2 | 8.87 | 16.1 |
| Calculated | 56.0 | 8.95 | 16.3 |

EXAMPLE III

Preparation of

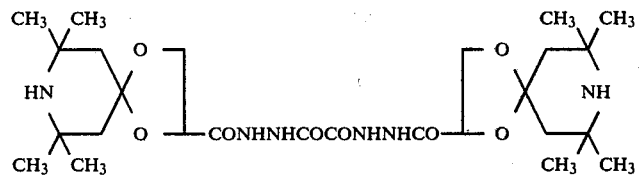

2.6 g of the compound prepared in Example II, 1.3 g of diphenyl oxalate and 15 ml of dioxane were heated and stirred for seven hours at temperatures up to 110° C.

After cooling, crystals precipitated and were filtered, washed with ethanol and dried. 2.1 g of pale yellow crystals, m.p. 265° to 270° C., was obtained.

IR Analysis
$\nu_{C=O}$: 1650 cm$^{-1}$, $\nu_{NH}$: 3340 cm$^{-1}$
$\nu_{C-O}$(ketal): 1105 cm$^{-1}$
Elemental Analysis:

|  | C % | H % | N % |
|---|---|---|---|
| Found | 55.0 | 7.71 | 14.8 |
| Calculated | 54.9 | 7.75 | 14.8 |

EXAMPLE IV

Preparation of

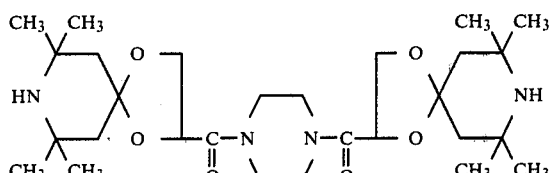

2.7 g of the compound prepared in Example I, 1.6 g of piperazine hexahydrate and 5 ml of dioxane were heated and stirred for fifteen hours under reflux.

After cooling, a powder precipitated and was filtered and dried. 1.9 g of pale yellow powder, m.p. 295° C. (decomposition), was obtained.

IR Analysis:
$\nu_{C=O}$: 1630 cm$^{-1}$, $\nu_{C-O}$(ketal): 1110 cm$^{-1}$
Elemental Analysis:

|  | C % | H % | N % |
|---|---|---|---|
| Found | 62.5 | 9.02 | 10.5 |
| Calculated | 62.7 | 8.96 | 10.4 |

The 2,2,6,6-tetrasubstituted-4piperidyl carboxylic acid esters and amides of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylontrile-styrene-butadiene copolymers, synthetic rubbers of all types, such as polychloroprene; polyvinyl halides, including polyvinyl chloride homopolymer; polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycolterephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex and foam.

The piperidyl carboxylic acid esters and amides of the invention can be used as a stabilizer in an amount within the range from about 0.001 to about 5 parts by weight, preferably from 0.05 to 3 parts by weight, per 100 parts by weight of resin.

The stabilizers of the invention can be employed as the sole stabilizer, or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylontrile-butadiene-styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention:

EXAMPLES 1 TO 14

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2.0 |
| Tris (nonyl phenyl) phosphite | 0.2 |
| Ca stearate | 1.0 |
| Zn stearate | 0.1 |
| Stabilizer as shown in Table I | 0.2 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for a total of fourteen stabilizers in accordance with the invention, having the formulae indicated in Table I, in comparison with two controls, 2,2,6,6-tetramethyl-4-piperidyl benzoate, and stearyl-2,2,6,6-tetramethylpiperidine-4-carboxylate. The following results were obtained:

TABLE I

| | Stabilizer | Hours to failure |
|---|---|---|
| Control | | |
| 1 | None | 180 |
| 2 | 2,2,6,6-Tetramethyl-4-piperidyl benzoate | 300 |
| 3 | Stearyl-2,2,6,6-tetramethyl piperidine-4-carboxylate | 330 |
| Example No. | | |
| 1 | [structure: 2,2,6,6-tetramethylpiperidine with spiro dioxy, —COOC$_{18}$H$_{37}$] | 620 |
| 2 | [structure: bis-piperidine spiro dioxy —COOCH$_2$—C≡ ]$_4$ | 750 |
| 3 | [structure: piperidine spiro dioxy —COO— piperidine] | 690 |
| 4 | [structure: piperidine spiro dioxy —CONHNHCOCONHNHCO— spiro dioxy piperidine] | 710 |

TABLE I-continued

| | Stabilizer | Hours to failure |
|---|---|---|
| 5 | 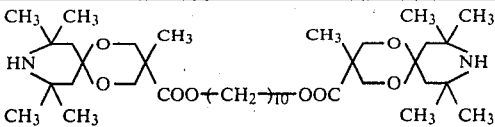 | 630 |
| 6 | 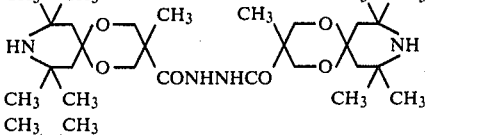 | 720 |
| 7 | 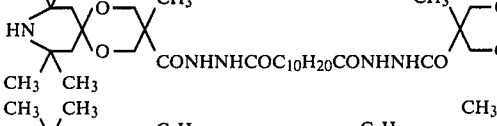 | 660 |
| 8 | 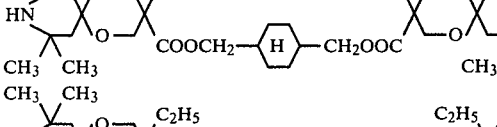 | 700 |
| 9 | 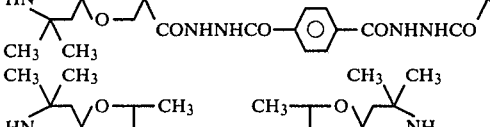 | 680 |
| 10 | 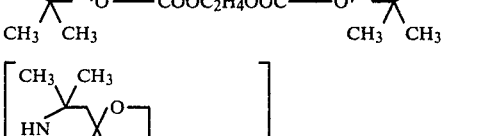 | 610 |
| 11 | 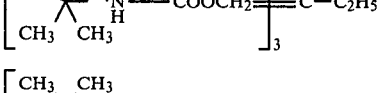 | 630 |
| 12 | 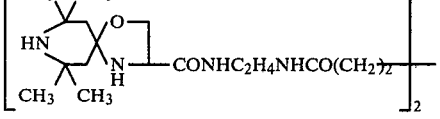 | 670 |
| 13 | 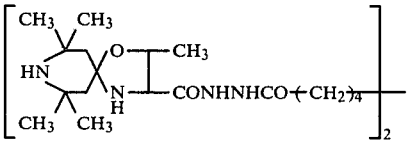 | 620 |
| 14 | 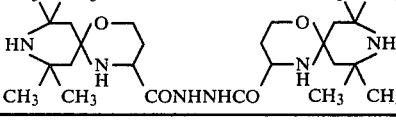 | 610 |

It is apparent that each of the stabilizers in accordance with the invention is far superior to the Controls, which are conventional ultraviolet light stabilizers for polyvinyl chloride.

EXAMPLES 15 TO 28

Polypropylene compositions were prepared using stabilizers of the invention and two of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table II | 0.3 |

The compositions were thoroughly blended in a Brabender Plastograph, and then compression-molded to form sheets 0.3 mm thick. Pieces 2.5 cm square were cut off from the sheets and exposed to a high voltage mercury lamp. Hours to failure was noted in comparison with two controls, 8-aza-7,7,9,9-tetramethyl-1,4-dioxaspiro-[4,5]-3-decylmethyl acetate and 9-aza-8,8,10,10-tetramethyl-1,5-dioxaspiro-[5,5]-undecane, and are shown in Table II.

TABLE II

| | Stabilizer | Hours to failure |
|---|---|---|
| Control | | |
| 1 | 8-Aza-7,7,9,9-tetramethyl-1,4-dioxaspiro-[4,5]-3-decylmethyl acetate | 280 |
| 2 | 9-Aza-8,8,10,10-tetramethyl-1,5-dioxaspiro-[5,5]-undecane | 310 |
| Example No. | | |
| 15 | [2,2,6,6-tetramethylpiperidine spiro dioxolane]—COOC$_2$H$_5$ | 620 |
| 16 | {[2,2,6,6-tetramethylpiperidine spiro dioxolane]—COOCH$_2$≡C}$_4$ | 770 |
| 17 | [piperidine-dioxolane]—CONH—C$_2$H$_4$—NHCO—[dioxolane-piperidine] | 640 |
| 18 | [piperidine-dioxolane]—CONHNHCOC$_2$H$_4$—[2,6-di-t-C$_4$H$_9$-4-OH-phenyl] | 630 |
| 19 | Two [piperidine-dioxane-CH$_3$]—COOC$_2$H$_4$— groups attached to isocyanurate (triazine trione) with third C$_2$H$_4$—OOC—[dioxane-piperidine] arm | 760 |
| 20 | [piperidine-dioxane-CH$_3$]—COO—[cyclohexyl—C(CH$_3$)$_2$—cyclohexyl]—OOC—[dioxane-piperidine] | 680 |
| 21 | [piperidine-dioxane-CH$_3$]—CONHNHC(O)—C(O)NHNHCO—[dioxane-piperidine] | 730 |
| 22 | [piperidine-dioxane-CH$_3$]—COOCH$_2$—C(CH$_3$)(CH$_3$)—CH$_2$OOC—[dioxane-piperidine] | 670 |

TABLE II-continued

| | Stabilizer | Hours to failure |
|---|---|---|
| 23 | [structure: bis-piperidyl with spiro O-C₂H₅ groups linked by CONH-(CH₂)ₙ-NHCO] | 710 |
| 24 | [structure: bis-piperidyl spiro linked by -COO-(CH₂)ₙ-OOC-] | 690 |
| 25 | [structure: bis-piperidyl spiro linked by -COO-(2,6-di-t-C₄H₉-phenyl)-OOC-] | 660 |
| 26 | [structure: bis-piperidyl spiro linked by -CONHNHCO-] | 680 |
| 27 | [structure: bis-piperidyl with spiro O-CH₃ linked by -CONH-(CH₂)₃-NHCO-] | 640 |
| 28 | [structure: bis-piperidyl spiro linked by -CONHNHCOCONHNHCO-] | 660 |

It is apparent from the above results that the compounds of the invention are superior stabilizer in enhancing the resistance of the polypropylene polymer composition to deterioration in the presence of ultraviolet light.

EXAMPLES 29 TO 42

Ethylene-vinyl acetate copolymer compositions were prepared using stabilizers of the invention and three of the prior art, and having the following formulation:

| Ingredient | Parts by Weight |
|---|---|
| Ethylene-vinylacetate copolymer | 100 |
| 2,6-di-t-butyl-p-cresol | 0.1 |
| Ca stearate | 0.1 |
| Zn stearate | 0.1 |
| 10 Diisodecylphenylphosphite | 0.2 |
| Stabilizer as shown in Table III | 0.3 |

The stabilizer was blended with the polymer on a two-roll mill at 130° C., and sheets 0.4 mm thick were then compression molded at 140° C. from the resulting blend. Pieces 2.5 cm square were cut off from the sheets and exposed to ultraviolet light in a Weather-O for 500 hours. At the start and at the conclusion of the test, tensile strength of the sheet samples were determined. The results in comparison with three controls, 2-hydroxy-4-methoxy benzophenone, bis-(2,2,6,6-tetramethyl-4-piperidyl) sebacate and benzoxazaline-2-spiro-4'-(2',2',6'6'-tetramethylpiperidine) are given in Table III as percent retention of the initially determined tensile strength:

TABLE III

| | Stabilizer | % Retention of tensile strength 500 hours |
|---|---|---|
| Control | | |
| 1 | 2-hydroxy-4-methoxy-benzophenone | 70 |
| 2 | Bis(2,2,6,6-tetramethyl-4-piperidyl) sebacate | 74 |
| 3 | Benzoxazoline-2-spiro-4'-(2',2',6',6'-tetramethyl piperidine) | 68 |
| Example No. | | |

TABLE III-continued
| | Stabilizer | % Retention of tensile strength 500 hours |
|---|---|---|
| 29 | 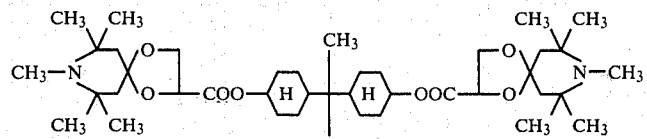 | 84 |
| 30 | 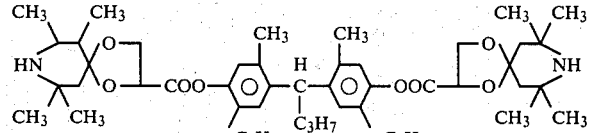 | 83 |
| 31 | 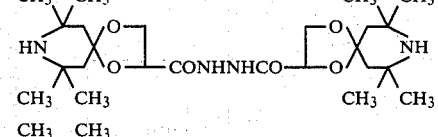 | 83 |
| 32 | 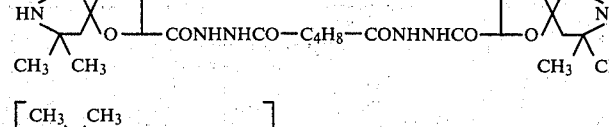 | 84 |
| 33 | 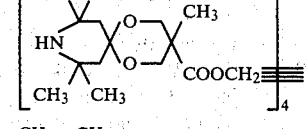 | 87 |
| 34 | 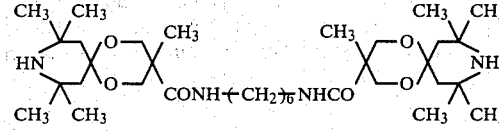 | 85 |
| 35 | 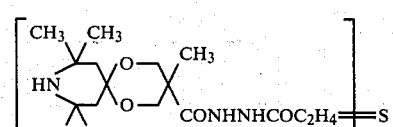 | 82 |
| 36 | 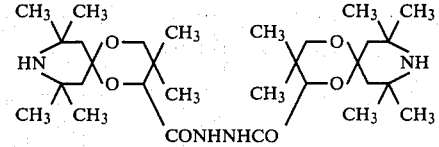 | 81 |
| 37 | 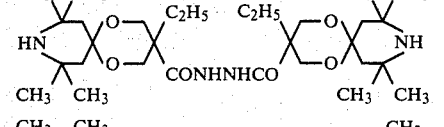 | 82 |
| 38 | 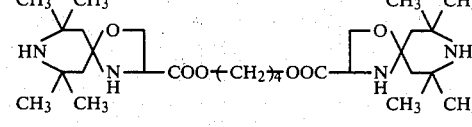 | 85 |
| 39 | 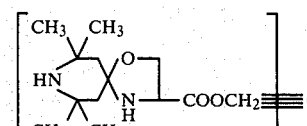 | 87 |

TABLE III-continued

| | Stabilizer | % Retention of tensile strength 500 hours |
|---|---|---|
| 40 | [structure: 2,2,6,6-tetramethyl-4-piperidyl with CH3N group, -CONH-phenyl] | 80 |
| 41 | [structure: bis-piperidyl with -CONHNHCOCONHNHCO- linker] | 86 |
| 42 | [structure: bis-piperidyl with -CH2CONH(CH2)6NHCOCH2- linker] | 83 |

It is apparent from the results that the stabilizer compositions in accordance with the invention are superior to 2-hydroxy-4-methoxy benzophenone, bis(2,2,6,6-tetramethyl-4-piperidyl) sebacate and benzoxazoline-2-spiro-4'-(2',2',6',6'-tetramethyl piperidine) in enhancing the resistance of the ethylene-vinyl acetate copolymer to deterioration in the presence of ultraviolet light.

EXAMPLES 43 to 54

High density polyethylene compositions were prepared using the stabilizers of the invention and three of the prior art, and having the following formulation:

| Ingredient | Parts by Weight |
|---|---|
| High-density polyethylene | 100 |
| Ca stearate | 1.0 |
| Tetrakis-(methylene-3-(3,5-di-t-butyl-4-hydroxyphenyl) propionate) methane | 0.1 |
| Distearylthiodipropionate | 0.3 |
| Stabilizer as shown in Table IV | 0.3 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV:

TABLE IV

| | Stabilizer | Hours to failure |
|---|---|---|
| Control | | |
| 1 | 2,4,6-Tris(2,2,6,6-tetramethyl-4-piperidylamino)-1,3,5-triazine | 700 |
| 2 | Bis(9-aza-8,8,10,10-tetramethyl-3-ethyl-1,5-dioxaspiro-[5,5]-3-undecylmethyl)adipate | 750 |
| 3 | 2(2'-Hydroxy-5'-methylphenyl)benzotriazole | 740 |
| Example No. | | |
| 43 | [structure: bis(2,2,6,6-tetramethyl-piperidyl-dioxy) with -COO(CH2)6OOC- linker] | 1390 |
| 44 | [structure: 2,2,6,6-tetramethyl-piperidyl-dioxy with -COO-phenyl] | 1220 |

TABLE IV-continued

| | Stabilizer | Hours to failure |
|---|---|---|
| 45 | (2,2,6,6-tetramethylpiperidin-4-yl) triester of 1,3,5-triazine-2,4,6-tricarbamate | 1410 |
| 46 | 2,2,6,6-tetramethylpiperidin-4-yl 2-methyl-2-(3,5-di-t-butyl-4-hydroxyphenyl)propanoate ester | 1250 |
| 47 | bis(2,2,6,6-tetramethylpiperidin-4-yl) ester of 2,2'-[oxalylbis(hydrazinocarbonyl)]bis(2-methylpropanoate) | 1480 |
| 48 | tetra(2,2,6,6-tetramethylpiperidin-4-yl) ester of 2-ethyl-2-(propargyloxymethyl)... | 1450 |
| 49 | bis(1,2,2,6,6-pentamethylpiperidin-4-yl) diester, methylenebis-carbamate linkage | 1330 |
| 50 | bis(2,2,6,6-tetramethylpiperidin-4-yl) ester, 1,3-cyclohexylene-bis(methylenecarbamate) | 1360 |
| 51 | tris(2,2,6,6-tetramethylpiperidin-4-yl) ester of 1,3,5-triazinane-1,3,5-tricarboxylate | 1420 |

TABLE IV-continued

| Stabilizer | Hours to failure |
|---|---|
| 52. Bis(2,2,6,6-tetramethyl-4-amino-piperidine) diester with HOOCCH₂O(CH₂)₆OCH₂COOH | 1400 |
| 53. Tetrakis(2,2,6,6-tetramethyl-4-amino-piperidine) tetraester of [CH₂COOCH₂—C≡]₄ | 1470 |
| 54. Bis(2,2,6,6-tetramethyl-4-amino-piperidine) with piperazine-dicarboxamide linker via propyl chains | 1320 |

The stabilizers of the invention are clearly superior to the controls in enhancing resistance of the polyethylene to degradation under ultraviolet light.

EXAMPLES 55 to 68

Acrylonitrile-butadiene-styrene terpolymer resin compositions were prepared using stabilizers of the invention and two of the prior art, and having the following formulation:

| Ingredient | Parts by Weight |
|---|---|
| Acrylonitrile-butadiene-styrene terpolymer | 100 |
| 4,4'-Butylidene-bis-(2-tert-butyl-m-cresol) | 0.1 |
| Stabilizer as shown in Table V | 0.3 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| | Stabilizer | % Tensile strength retained |
|---|---|---|
| Control | | |
| 1 | 2,4-Dihydroxybenzophenone | 55 |
| 2 | Pentaerythritol tetrakis (2,2,6,6-tetramethyl-4-hydroxy-piperidine-4-carboxylate) | 63 |
| Example No. | | |
| 55 | Tris(2,2,6,6-tetramethyl-4-hydroxy-piperidine) triester with [—COOCH₂—C≡C—C₂H₅]₃ | 88 |
| 56 | Tetrakis(2,2,6,6-tetramethyl-4-hydroxy-piperidine) tetraester with [—COOCH₂—C≡C]₄ | 93 |

TABLE V-continued

| | Stabilizer | % Tensile strength retained |
|---|---|---|
| 57 | (2,2,6,6-tetramethylpiperidin-4-yl) spiro-ketal with (2,2,6,6-tetramethylpiperidin-4-yl) ester of —COO— | 91 |
| 58 | bis-spiroketal linked via —COOC$_2$H$_4$OOC—C$_6$H$_4$—COOC$_2$H$_4$OOC— | 84 |
| 59 | spiroketal—CONHNHCO—(2-hydroxyphenyl) | 83 |
| 60 | spiroketal with —C(CH$_3$)—COOC$_{12}$H$_{25}$ | 83 |
| 61 | [spiroketal—C(CH$_3$)—COOCH$_2$—C≡]$_4$ | 90 |
| 62 | spiroketal—C(CH$_3$)—CONHNHCO—(3,5-di-t-C$_4$H$_9$-4-OH-phenyl) | 86 |
| 63 | [spiroketal—C(CH$_3$)(CH$_3$)—COOCH$_2$—C≡]$_4$ | 89 |
| 64 | [spiro-N,O-ketal—COOCH$_2$—C≡]$_4$ | 90 |

TABLE V-continued

| | Stabilizer | % Tensile strength retained |
|---|---|---|
| 65 | [bis-piperidinyl structure with -CONHNHCO- linked to benzene -CONHNHCO- bis-piperidinyl] | 87 |
| 66 | [piperidinyl-O-CH3 with -COOCH2-C≡ ]4 | 88 |
| 67 | [piperidinyl with -COOCH2-C≡CH2 ]4 | 86 |
| 68 | [bis-piperidinyl structure with -COOC2H4-N(piperazine)N-C2H4OOC-] | 85 |

It is apparent from the data that the stabilizers of the invention are superior to the stabilizers of the prior art.

EXAMPLES 69 to 79

Polybutylene terephthalate resin formulations were prepared having the following composition:

| Ingredient | Parts by Weight |
|---|---|
| Polybutylene terephthalate | 100 |
| 1,3,5-trimethyl-2,4,6-tris(3,5-di-t-butyl-4-hydroxybenzyl)benzene | 0.1 |
| Stabilizer as shown in Table VI | 0.2 |

The compositions were extruded to form pellets, and then test pieces were molded from the pellets by injection molding at 270° C. The test pieces were irradiated with ultraviolet light for 500 hours in a Weather-O-Meter. Tensile strength before and after exposure was determined, and the percent tensile strength retained after the exposure is given in Table VI.

TABLE VI

| | Stabilizer | % Retention of tensile strength |
|---|---|---|
| Control | | |
| 1 | 9-Aza-8,8,10,10-tetramethyl-3-ethyl-1,5-dioxaspiro-[5,5]-3-undecylmethyl acetate | 44 |
| 2 | 2-Hydroxy-4-octoxybenzophenone | 52 |
| Example No. | | |
| 69 | [piperidinyl-dioxaspiro structure with -COOC2H5] | 83 |

TABLE VI-continued

| | Stabilizer | % Retention of tensile strength |
|---|---|---|
| 70 | [piperidine-CH(CH3)2-O-CO-O-COOCH2≡C-CH2-O]2 (bis-2,2,6,6-tetramethylpiperidinyl derivative) | 85 |
| 71 | bis(2,2,6,6-tetramethylpiperidinyl) piperazine-1,4-dicarbonyl diester | 89 |
| 72 | 2,2,6,6-tetramethylpiperidinyl-O-CONHNHCO-C6H4-COOCH3 | 85 |
| 73 | 2,2,6,6-tetramethylpiperidinyl-O-C(CH3)-CONH-C4H9 | 83 |
| 74 | bis(2,2,6,6-tetramethylpiperidinyl-O-C(CH3))-CONHNHCOC10H20CONHNHCO- | 90 |
| 75 | bis(2,2,6,6-tetramethylpiperidinyl-O-C(C2H5))-CONHNHCO-C6H4-CONHNHCO- | 88 |
| 76 | 2,2,6,6-tetramethylpiperidinyl-NH-COOC4H9 | 82 |
| 77 | bis(2,2,6,6-tetramethylpiperidinyl-NH)-CONHNHCO- | 87 |
| 78 | [2,2,6,6-tetramethylpiperidinyl-NH-C(CH3)-COOC2H4-S]2 | 84 |

TABLE VI-continued

| | Stabilizer | % Retention of tensile strength |
|---|---|---|
| 79 | [Structure: bis-(2,2,6,6-tetramethylpiperidine with HN and O, -CH₂CONH-C₆H₄-NHCO-)₂] | 86 |

It is apparent that the stabilizers of the invention are more effective ultraviolet light stabilizers for polybutylene terephthalate resins than the stabilizers of the prior art.

EXAMPLES 80 to 88

Polyurethane resin compositions were prepared using stabilizers of the invention and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6,di-t-butyl-p-cresol | 0.1 |
| Stabilizer as shown in Table VII | 0.3 |

[1]A polyurethane-isocyanurate made from toluene diisocyanate and alkylene polyol.

The stabilizer was blended with the finely powdered polyurethane resin on a two-roll mill for five minutes at 70° C., and the sheet was then compression molded at 120° C. for five minutes to form sheets 0.5 mm thick. Pieces 2.5 cm square were cut out from the sheets, and exposed to ultraviolet light in a Weather-O-Meter for thirty hours.

Tensile strength before and after exposure was determined, and the percent tensile strength retained after the exposure is given in Table VII.

TABLE VII

| | Stabilizer | % Retention of tensile strength |
|---|---|---|
| Control | | |
| 1 | N,N'-bis(2,2,6,6-tetramethyl-4-piperidyl)oxalamide | 60 |
| 2 | 8-Aza-7,7,9,9-tetramethyl-1,4-dioxaspiro-[4,5]-decane | 52 |
| Example No. | | |
| 80 | [Structure: 8-aza-7,7,9,9-tetramethyl-1,4-dioxaspiro[4,5]decane with -COOC₁₈H₃₇] | 72 |
| 81 | [Structure: 8-aza-7,7,9,9-tetramethyl-1,4-dioxaspiro[4,5]decane with -CONHNH₂] | 74 |
| 82 | [Structure: bis(8-aza-7,7,9,9-tetramethyl-1,4-dioxaspiro[4,5]decane) linked by -CONHNHCOCONHNHCO-] | 82 |
| 83 | [Structure: 8-aza-7,7,9,9-tetramethyl-1,4-dioxaspiro[4,5]decane with -CONHC₂H₄NHCOCH₃] | 74 |

| | Stabilizer | % Retention of tensile strength |
|---|---|---|
| 84 | 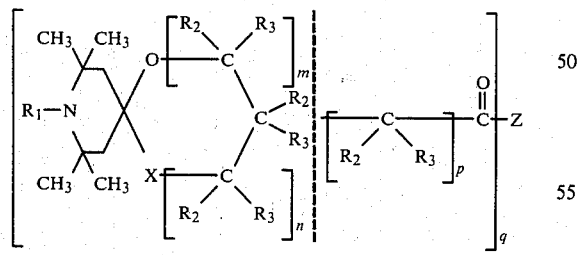 (structure) | 80 |
| 85 | | 71 |
| 86 | | 78 |
| 87 | | 77 |
| 88 | | 79 |

The stabilizers of the invention are clearly superior to the controls in enhancing resistance of the polyurethane resin to degradation under ultraviolet light.

Having regard to the foregoing disclosure, the following is claimed as patentable and inventive embodiments thereof:

1. 2,2,6,6-Tetramethyl-4-piperidyl carboxylic acid esters and amides having the general formula:

wherein:

$R_1$, $R_2$ and $R_3$ are selected from the group consisting of hydrogen and alkyl having from one to about eighteen carbon atoms;

X is oxygen or imino >NH;

m is zero, 1 or 2;

n is zero, 1 or 2;

m+n is 1 or 2;

p is zero or 1;

q is 1 to 6;

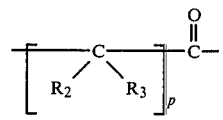

is linked to carbon in place of one $R_2$ or $R_3$ group; and

Z is selected from the group consisting of:

(a) $OR_5$ where $R_5$ is alkyl, aryl or cycloalkyl having one to twenty-four carbon atoms and hydroxy-, carboxy- and oxy-substituted such groups having from one to five OH or O groups; and 2,2,6,6-tetramethyl-4-piperidyl;

(b) $OR_6O$ where $R_6$ is alkylene, arylene or cycloalkylene having one to twenty-four carbon atoms and hydroxy-substituted such groups having one to four OH groups; $R_6$ alkylene, arylene or cycloalkylene can include oxyether —O— and thioether —S— linking groups attached to alkylene, arylene or cycloalkylene groups as in polyoxyalkylene and polythioalkylene groups and polyoxyalkylene arylene groups having from one to about five oxy or thio groups and from two to about six alkylene groups having from two to about six carbon atoms;

(c)

where $R_6$ is alkylene, arylene or cycloalkylene having one to twenty-four carbon atoms and hydroxy-substituted such groups having one to four OH groups;

$R_6$ alkylene, arylene or cycloalkylene can include oxyether —O— and thioether —S— linking groups attached to alkylene, arylene or cycloalkylene groups as in polyoxyalkylene and polythioalkylene groups and polyoxyalkylene arylene groups having from one to about five oxy or thio groups and from two to about six alkylene groups having from two to about six carbon atoms; $R_7$ is alkyl, aryl or cycloalkyl having one to twenty-four carbon atoms and hydroxy-substituted such groups having from one to five OH groups;

(d) $NHR_5$ where $R_5$ is alkyl, aryl or cycloalkyl having one to twenty-four carbon atoms and amino-substituted such groups having from one to five amino groups;

(e)

where $R_6$ is alkylene, arylene or cycloalkylene having one to twenty-four carbon atoms and amino-substituted such groups having one to four amino groups; $R_7$ is alkyl, aryl or cycloalkyl having one to twenty-four carbon atoms and amino-substituted such groups having one to five amino groups;

(f)   —$NHNH_2$;   —NHNH—;   —NHNH-COCONHNH$_2$; —NHNHCOR$_7$; —NHNHCOR$_6$-CONHNH$_2$;   —NHNHCOR$_6$CONHNH—; —NHNHCOCONHNH—$_1$;   —NHR$_6$NH$_2$—; —NHR$_6$NH—; NHR$_6$NHCOR$_6$CONHR$_6$NH;

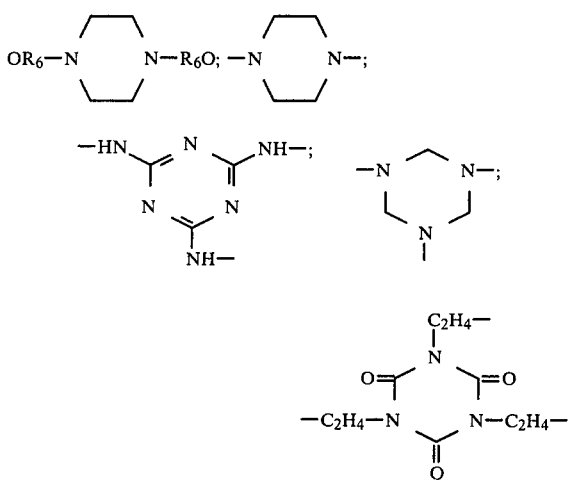

where $R_6$ is alkylene, arylene or cycloalkylene having one to twenty-four carbon atoms and amino-substituted such groups having one to four amino groups; and such groups including oxyether and thioether linking groups as in (b) above, and $R_7$ is as in (c) above.

2. A compound according to claim 1 having the general formula:

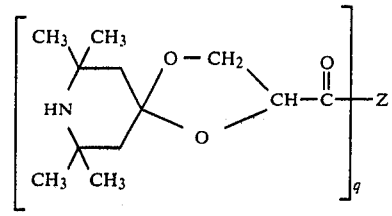

wherein Z is as in claim 1.

3. A compound according to claim 1 having the general formula:

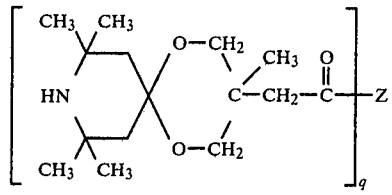

wherein Z is as in claim 1.

4. A compound according to claim 1 having the general formula:

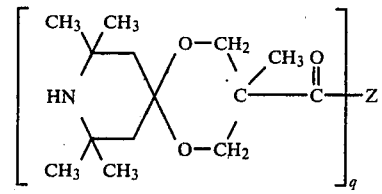

wherein Z is as in claim 1.

5. A compound according to claim 1 in which $R_1$, $R_2$ and $R_3$ are hydrogen.

6. A compound according to claim 1 in which X is NH.

7. A compound according to claim 1 having the general formula:

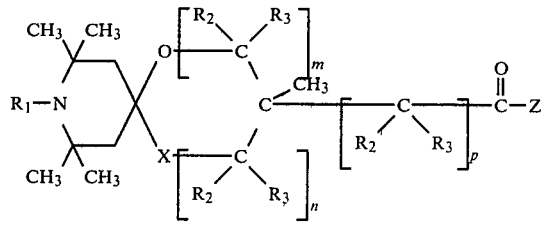

wherein $R_1$, $R_2$ and $R_3$, X, m, n, p and Z are as in claim 1.

8. A compound according to claim 1 in which Z is $OR_5$, where $R_5$ is selected from the group consisting of alkyl, aryl and cycloalkyl having from one to twenty-four carbon atoms and hydroxy-substituted such groups having from one to five OH groups.

9. A compound according to claim 1 in which Z is

where R₆ is selected from the group consisting of alkylene, arylene, and cycloalkylene having one to twenty-four carbon atoms and hydroxy-substituted such groups having one to four OH groups; polyoxyalkylene and polythioalkylene having from one to about five oxy or thio groups and from two to about six alkylene groups having from two to about six carbon atoms; and R₇ is alkyl, aryl or cycloalkyl having one to twenty-four carbon atoms and hydroxy-substituted such groups having from one to five OH groups.

10. A compound according to claim 1 in which Z is NHR₅ where R₅ is selected from the group consisting of alkyl, aryl and cycloalkyl having one to twenty-four carbon atoms and amino-substituted such groups having from one to five amino groups.

11. A compound according to claim 1 in which Z is

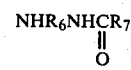

where R₆ is selected from the group consisting of alkylene, arylene and cycloalkylene having one to twenty-four carbon atoms and amino-substituted such groups having one to four amino groups; and R₇ is selected from the group consisting of alkyl, aryl and cycloalkyl having one to twenty-four carbon atoms and amino-substituted such groups having one to five amino groups.

12. A compound according to claim 1 in which q is 1.
13. A compound according to claim 1 in which q is 2.
14. A compound according to claim 1 in which q is 2 and Z is —NHNH—.
15. A compound according to claim 1 in which q is 1 and Z is NHNH₂.
16. A compound according to claim 1 in which q is 3 and Z is

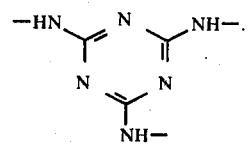

17. A compound according to claim 1 in which q is 2 and Z is NHNHCOCONHNH.

18. A compound according to claim 17 in which q is 3 and Z is

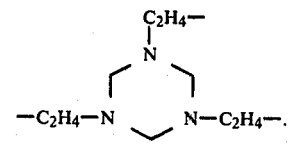

19. A compound according to claim 1 having the formula:

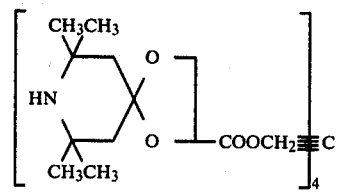

20. A compound according to claim 1 having the formula:

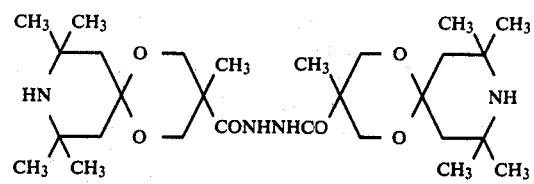

21. A compound according to claim 1 having the formula:

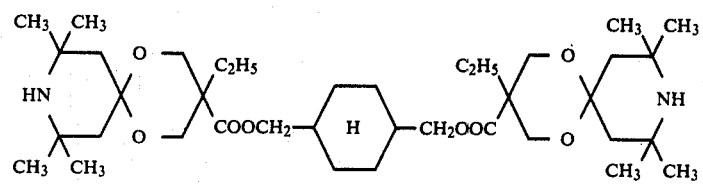

22. A compound according to claim 1 having the formula:

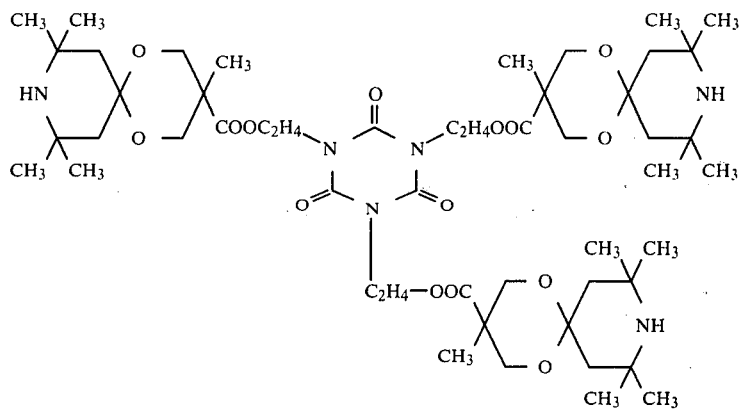

23. A compound according to claim 1 having the formula:

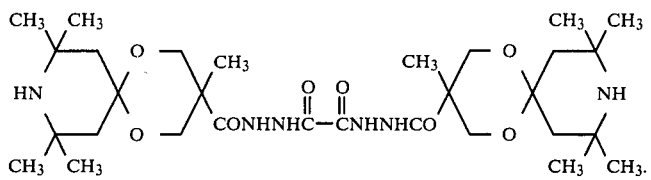

24. A polyvinyl chloride resin composition having improved resistance to deterioration when heated at 350° F., comprising a polyvinyl chloride resin and a compound in accordance with claim 1.

25. A polyvinyl chloride resin composition in accordance with claim 24, in which the polyvinyl chloride resin is polyvinyl chloride homopolymer.

26. A polyvinyl chloride resin composition in accordance with claim 24, in which the polyvinyl chloride resin is a copolymer of vinyl chloride and vinyl acetate.

27. An olefin polymer composition having improved resistance to deterioration comprising an olefin polymer selected from the group consisting of polymers of alpha-olefins having from two to six carbon atoms and polystyrene, and a compound in accordance with claim 1.

28. An olefin polymer composition in accordance with claim 24 wherein the polyolefin is polypropylene.

29. An olefin polymer composition in accordance with claim 24 wherein the polyolefin is polyethylene.

30. An acrylonitrile-butadiene-styrene polymer having its resistance to deterioration when heated at 300° F. and above enhanced by a compound in accordance with claim 1.

31. A polyester polymer composition having improved resistance to deterioration comprising a polyester polymer and a compound in accordance with claim 1.

32. A polyurethane resin composition having improved resistance to deterioration comprising a polyurethane resin and a compound in accordance with claim 1.

33. An ethylene-vinyl acetate copolymer composition having improved resistance to deterioration comprising an ethylene-vinyl acetate copolymer and a compound in accordance with claim 1.

* * * * *